United States Patent [19]

Katz et al.

[11] Patent Number: 5,952,392
[45] Date of Patent: Sep. 14, 1999

[54] LONG-CHAIN ALCOHOLS, ALKANES, FATTY ACIDS AND AMIDES IN THE TREATMENT OF BURNS AND VIRAL INHIBITION

[75] Inventors: David H. Katz, La Jolla; Laura E. Pope, Carlsbad; Mohammed H. Khalil; John F. Marcelletti, both of San Diego; Lee R. Katz, La Jolla, all of Calif.

[73] Assignee: Avanir Pharmaceuticals, San Diego, Calif.

[21] Appl. No.: 08/916,624

[22] Filed: Aug. 22, 1997

Related U.S. Application Data

[60] Provisional application No. 60/064,850, Sep. 17, 1996.

[51] Int. Cl.$^6$ ............................ A01N 31/00; A61F 13/00
[52] U.S. Cl. ...................... 514/724; 514/936; 424/434; 424/435
[58] Field of Search ................... 514/724, 936; 424/434, 435

[56] References Cited

U.S. PATENT DOCUMENTS

| | | | |
|---|---|---|---|
| 1,109,119 | 9/1914 | Ellis . | |
| 3,592,930 | 7/1971 | Katz et al. | 424/243 |
| 3,946,035 | 3/1976 | Jacquet et al. | 260/243 |
| 3,987,198 | 10/1976 | Young | 424/320 |
| 4,025,645 | 5/1977 | Jelenko, III | 424/312 |
| 4,076,799 | 2/1978 | Willer et al. | 424/45 |
| 4,186,211 | 1/1980 | Debat | 424/343 |
| 4,200,655 | 4/1980 | Farah et al. | 424/343 |
| 4,258,029 | 3/1981 | Moloney et al. | 424/88 |
| 4,513,008 | 4/1985 | Revici et al. | 514/560 |
| 4,624,966 | 11/1986 | Yamamoto et al. | 514/724 |
| 4,670,471 | 6/1987 | Clark | 514/724 |
| 4,684,479 | 8/1987 | D'Arrigo | 252/307 |
| 4,865,848 | 9/1989 | Cheng et al. | 424/449 |
| 4,874,794 | 10/1989 | Katz | 514/724 |
| 4,879,109 | 11/1989 | Hunter | 424/83 |
| 4,900,555 | 2/1990 | Cheng et al. | 424/449 |
| 4,940,586 | 7/1990 | Cheng et al. | 424/464 |
| 4,950,688 | 8/1990 | Bowser et al. | 514/847 |
| 4,956,171 | 9/1990 | Chang | 424/449 |
| 5,030,448 | 7/1991 | Hunter | 424/83 |
| 5,070,107 | 12/1991 | Katz | 514/724 |
| 5,071,879 | 12/1991 | Katz | 514/724 |
| 5,104,656 | 4/1992 | Seth et al. | 424/401 |
| 5,154,855 | 10/1992 | Sekiguchi et al. | 252/312 |
| 5,166,219 | 11/1992 | Katz | 514/724 |
| 5,194,451 | 3/1993 | Katz | 514/724 |
| 5,208,257 | 5/1993 | Kabara | 514/552 |
| 5,216,142 | 6/1993 | Horrobin et al. | 514/50 |
| 5,276,020 | 1/1994 | Horrobin et al. | 514/45 |
| 5,380,754 | 1/1995 | Miller et al. | 514/513 |
| 5,436,234 | 7/1995 | Eibl | 514/77 |
| 5,534,554 | 7/1996 | Katz et al. | 514/724 |

FOREIGN PATENT DOCUMENTS 2569108  9/1990  France .
WO8807866  10/1988  WIPO .
WO9004388  5/1990  WIPO .
WO9602244A1  2/1996  WIPO .

OTHER PUBLICATIONS

Antonian, et al., (1987) AL721, A Novel Membrane Fluidizer, *Neuroscience & Biobehavioral Reviews*, 11:399–413.
Ferreira, et al., (1990) Inhibition of lipolysis by hydrocarbons and fatty alcohols, *J. Lipid Res.*, 31:889–897.
Banzan, Nicolas G., (1989) The Metabolism of Omega–3 Polyunsaturated Fatty Acids in the Eye: The Possible Role of Docosahexaenoic Acid and Docosanoids in Retinal Physiology and Ocular Pathology, *Prog. Clin. Biol. Res.*, 312:95–112.
McBride, et al., (1987) Evaluation of Triacontanol–Containing Compounds as Anti–Inflammatory Agents Using Guinea Pig Models, *J. of Investigative Dermatology*, 89(4):380–383.
Marcelletti, et al., (1992) B Cell Activator, Effects on B Cell Expression of CD23, Proliferation, and Antibody Secretion, *J. Immunol.*, 148(12):3857–3863.
Katz, et al., (1991) Antiviral activity of 1–docosanol, an inhibitor of lipid–enveloped viruses including herpes simplex, *Proc. Natl. Acad. Sci. USA*, 88:10825–10829.
Katz, et al., (1994) n–Docosanol: Broad Spectrum Anti–Viral Activity against Lipid–enveloped Viruses, *Annals N.Y. Acad. Sciences*, 724:472–488.
Morgan, et al. (1968) Electron Microscopy of Herpes Simplex Virus, I. Entry, *J. Virol.* 2(5):507–516.
Sandra, et al. (1979) Liposome–Cell Interactions, *J. Biol. Chem.* 254(7):2244–2249.
Sands, et al. (1979) Extreme Sensitivity of Enveloped Viruses, Including Herpes Simplex, to Long–Chain Unsaturated Monoglycerides and Alcohols, *Antimicrobial Agents and Chemotherapy*, 15(1):67–73.
Skehan, et al. (1990) New Colorimetric Cytotoxicity Assay for Anticancer–Drug Screening, *J. Natl. Cancer Inst.*, 82(13):1107–1112.
Snipes, et al., (1977) Inactivation of Lipid–Containing Viruses by Long–Chain Alcohols, *Antimicrob. Agents & Chemother.*, 11:98–104.
Stetten, D., Jr., (1942) Metabolism of a paraffin, *J. Biol. Chem.*, 136(147):327–332.

*Primary Examiner*—Mukund J. Shah
*Assistant Examiner*—Tamthom T. Ngo
*Attorney, Agent, or Firm*—Knobbe, Martens Olson & Bear, LLP

[57] ABSTRACT

Therapeutic compositions including a nonionic surfactant combined with long chain fatty acids, alkanes, amides or mono-unsaturated alcohols, particularly stearyl alcohol, erucyl alcohol, brassidyl alcohol, arachidyl alcohol, n-docosane, n-docosanoic acid, erucamide and stearic acid, or mixtures thereof, as active ingredients are disclosed. Methods of preventing or treating viral infections, treating skin or membrane inflammation or inhibiting cell proliferation using such compositions are disclosed.

20 Claims, 7 Drawing Sheets

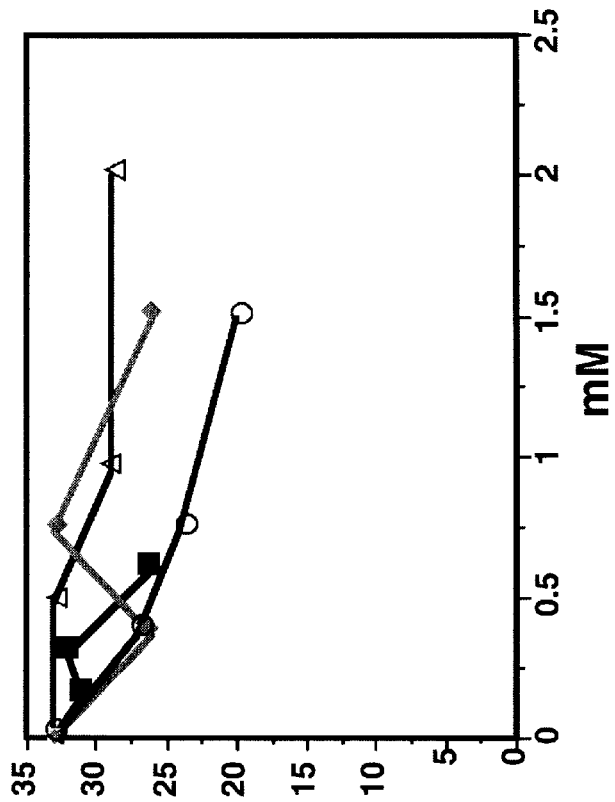
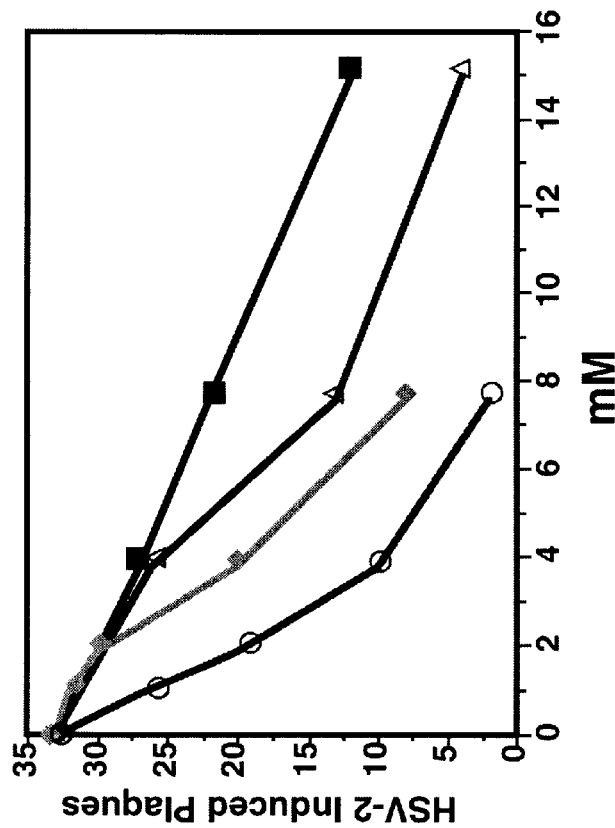
FIG. 2B
FIG. 2A

LONG-CHAIN ALCOHOLS, ALKANES, FATTY ACIDS AND AMIDES IN THE TREATMENT OF BURNS AND VIRAL INHIBITION

This application claims priority of Provisional Application 60/064,850, filed on Sep. 17, 1996.

FIELD OF THE INVENTION

This invention relates to therapeutic treatment of viral infections and skin inflammation using long chain fatty acids, long chain alkanes, amides and mono-unsaturated long chain alcohols, particularly by application of therapeutic compositions containing a nonionic surfactant and stearyl alcohol, erucyl alcohol, erucamide, brassidyl alcohol, arachidyl alcohol, n-docosanol, n-docosane, n-docosanoic acid or stearic acid as active ingredients.

BACKGROUND OF THE INVENTION

Viral infections cause considerable discomfort, disease and can be fatal. Viruses such as herpes simplex viruses (HSV-1 and HSV-2), cytomegalovirus (CMV), Epstein-Barr virus (EBV), varicella zoster virus (VZV), influenza viruses, human lymphotrophic viruses (e.g., HTLV-1) and human immunodeficiency viruses (e.g., HIV-1) result in significant morbidity and mortality. HSV-1 and HSV-2 are associated with inflammation and lesions of the skin and mucosal membranes, including cold sores, fever blisters and genital herpes lesions. VZV causes shingles and EBV is associated with mononucleosis. Influenza viruses cause flu symptoms and can be fatal. HIV causes acquired immunodeficiency which debilitates and kills infected individuals. Although these viruses may remain latent in some cells and for varying periods of time, generally viral replication results in irreversible destruction of the infected cell producing different clinical manifestations of the diseases they cause.

Antiviral and anti-inflammatory activities of aliphatic alcohols having from 20 to 32 carbons are known in the art as disclosed in U.S. Pat. No. 4,874,794, U.S. Pat. No. 5,071,879, U.S. Pat. No. 5,166,219, U.S. Pat. No. 5,194,451 and U.S. Pat. No. 5,534,554. Compositions containing aliphatic alcohols and related compounds having therapeutic activities are disclosed therein.

A C22 aliphatic alcohol, n-docosanol, suspended in a surfactant exhibits potent antiviral activity against viruses including herpes simplex virus, HIV-1 and respiratory syncytial virus in vitro and Friend virus in vivo (Katz, D. H., et al., *Proc. Natl. Acad. Sci. USA* 88:10825–10829, 1991; U.S. Pat. No. 5,534,554). Although the mechanism for this viral inhibition is unknown, n-docosanol does not inactivate the virus directly and thus is unlike C10 to C18 unsaturated alcohols that exhibit detergent-like antiviral activity (Katz, D. H., et al., *Proc. Natl. Acad. Sci. USA* 88:10825–10829, 1991; Snipes, W. et al., *Antimicrob. Agents Chemother.* 11:98–104, 1977). Progressive binding and uptake of n-docosanol by cells may account for its antiviral activity because pre-incubation of cells with the alcohol produces optimal antiviral activity. During incubation, 70% of the cell-associated n-docosanol is found in cell membranous components and the remainder is associated with soluble cell fractions (Katz, D. H., et al., *Proc. Natl. Acad. Sci. USA* 88:10825–10829, 1991). Cell membrane incorporation of n-docosanol does not inhibit virus binding to the cell surface. Instead, early viral protein synthesis is inhibited more than 80% and viruses do not localize to nuclei (Marcelletti, J. F. et al., *Drugs of the Future* 17(19): 879–882, 1992).

Although intracellular metabolic conversions of n-docosanol may account for its antiviral activity (Katz, D. H. et al., *Annals N.Y. Acad. Sciences,* 724:472–488, 1994), the alcohol is not cytotoxic in concentrations up to 300 mM.

Inactivation of viruses has been reported using C14 to C20 unsaturated long chain alcohols having one to four unsaturated bonds. The most effective was γ-linolenyl alcohol, a C18 alcohol with double bonds at positions 6, 9 and 12; whereas a C18 alcohol with one cis double bond and a C20 alcohol with four double bonds were significantly less effective (Sands et al., Antimicrob. Agents & Chemother. 15:67–73, 1979). Compositions containing oleic acid (C18, one double bond) have been reported as effective for antiherpes virus agents (PCT patent application WO 9602244A1).

Some compounds that are structurally related to long-chain aliphatic alcohols also have been associated with antiviral activity. For example, U.S. Pat. No. 4,513,008 discloses the virucidal activity of C20 to C24 linear polyunsaturated acids, aldehydes or alcohols having five to seven double bonds. Compounds having a long chain fatty acyl group, containing at least three or four unsaturated bonds, attached to a nucleoside or nucleoside analogue are disclosed as antiviral treatments in U.S. Pat. No. 5,216,142. Related U.S. Pat. No. 5,276,020 discloses antiviral compounds having a C16, C18 or C20 long chain fatty acid group attached to a nucleoside analogue and a method of treating virus infection using these compounds.

Biological activity useful for treating tumors, protozoal and fungal diseases, autoimmune disease and bone marrow damage has been attributed to phospholipids having erucyl- and brassidyl-side chains, such as erucylphosphocholine (U.S. Pat. No. 5,436,234).

Although some long chain fatty alcohols and fatty acids affect cellular growth, such effects are presently ill-defined. For example, n-hexacosanol, a C26 alcohol, promotes neuronal growth whereas other long chain fatty n-alcohols containing 16, 20, 22, 24 and 30 carbon atoms do not (Borg, J. et al., *FEBS Lett.* 213(2):406–410, 1987). Docosahexaenoic acid, a C22 fatty acid having six double bonds, is concentrated in the central nervous system and the retina although its physiological role has not been defined (Bazan, N., *Prog. Clin. Biol. Res.* 312:95–112, 1989).

Antiviral activity has been reported for liposomal AL721, a mixture of neutral glycerides, phophatidylcholine and phosphatidylethanolamine (Antonian, L. et al., *Neurosci. Biobehav. Rev.* 11:399–413, 1987). Antimicrobial compositions for topical treatment containing a C15 glycerol monoester of lauric acid or a polyhydric alcohol monoester of lauric acid with a mixture of fatty acids (C10 capric and C8 caprylic acids) are disclosed in U.S. Pat. No. 5,208,257.

A method of preventing or reducing skin irritation by applying a protective agent containing polymers of C12 to C26 fatty acids prior to exposure to an allergenic agent is disclosed in U.S. Pat. No. 4,076,799. The preferred polymers have two to four carboxy or carboxyl salt groups, preferably the triethanolamine salt of dimerized linoleic acid or its saturated derivative. Other anti-inflammatory polymers containing aromatic heterocyclic residues or acyl residues in homopolymers or heteropolymers (e.g., vinyl esters of C8 to C18 fatty acids; m.w. 2,000 to 1,000,000) and having greater activity than the component monomers have been disclosed in U.S. Pat. No. 3,946,035.

Therapeutic treatment of herpes lesions using topically administered compositions containing an anesthetic, a surfactant and a topical carrier is disclosed in U.S. Pat. No.

5,380,754. A method of treating inflammation by topically applying ethyl-cis,cis(9,12)octadecadienoate (ethyl linoleate) is disclosed in U.S. Pat. No. 4,025,645 as a cold sore treatment.

The present invention discloses antiviral and cytotoxic effects of compounds related to long-chain aliphatic alcohols, including alkanes, alcohols, amides and long-chain fatty acids, and particularly compounds related to n-docosanol. These related compounds having antiviral activity include n-docosane, n-docosanoic acid, stearic acid, erucyl alcohol, erucamide and brassidyl alcohol. Moreover, the optimal ratio of surfactant to active ingredient for formulating an effective antiviral and/or cytotoxic suspension with these compounds or with n-docosanol is disclosed. These compounds and formulations are useful in antiviral preventive compositions and treatment therapeutics.

SUMMARY OF THE INVENTION

The present invention discloses antiviral and cytotoxic effects of compounds related to long-chain aliphatic alcohols, particularly related to n-docosanol. These related compounds having antiviral activity include n-docosane, n-docosanoic acid, stearic acid, erucyl alcohol, erucamide and brassidyl alcohol. Moreover, the optimal surfactant to aliphatic alcohol ratio for formulating an effective antiviral suspension is disclosed. These compounds and formulations are useful in antiviral preventive compositions and treatment therapeutics.

According to the invention, there is provided a composition comprising a nonionic surfactant and an active ingredient selected from the group consisting of stearyl alcohol, erucyl alcohol, brassidyl alcohol, arachidyl alcohol, n-docosanol, n-docosane, n-docosanoic acid, erucamide and stearic acid, or mixtures thereof, wherein the nonionic surfactant is a difunctional block-polymer that is a polyoxyalkylene derivative of propylene glycol having a molecular weight of about 1,000 to about 25,000, an octoxynol or deoxycholate, and wherein the nonionic surfactant and the active ingredient are present in a ratio of about 1:1 (w:w) to about 10:1 (w:w) in a pharmaceutically acceptable diluent or carrier. In one embodiment, the nonionic surfactant is a difunctional block-polymer that is a polyoxyalkylene derivative of propylene glycol having a molecular weight of about 25,000. In another embodiment, the nonionic surfactant is a block copolymer of ethylene oxide and propylene oxide having a molecular weight of about 8,400. In a preferred embodiment, the nonionic surfactant is octoxynol-9, octoxynol-10 or a combination thereof. In one embodiment, the ratio of nonionic surfactant to active ingredient is about 5:1 (w:w) to about 10:1 (w:w). Preferrably, the nonionic surfactant combined with n-docosanol in ratio of about 4:1 (w:w) to about 10:1 (w:w). In another preferred embodiment, the composition comprises the nonionic surfactant combined with stearic acid in ratio of about 4:1 (w:w) to about 10:1 (w:w). In a preferred embodiment, the composition comprises the nonionic surfactant combined with stearic acid in ratio of about 4:1 (w:w) to about 10:1 (w:w). In another embodiment, the composition comprises a surfactant that is a block copolymer of ethylene oxide and propylene oxide having a molecular weight of about 8,400 combined with n-docosanol in ratio of about 5:1 (w:w). In another preferred embodiment, the composition comprises a surfactant that is a difunctional block polymer that is a polyoxyalkylene derivative of propylene glycol having a molecular weight of about 25,000 combined with n-docosanol in ratio of about 5:1 (w:w).

According to another aspect of the invention, there is provided a composition consisting essentially of stearic acid and a nonionic surfactant, wherein the nonionic surfactant and the stearic acid are present in a ratio of about 1:1 (w:w) to about 10:1 (w:w) to form a suspension in a pharmaceutically acceptable diluent or carrier.

According to another aspect of the invention, there is provided a composition consisting of stearic acid and a nonionic surfactant, wherein the nonionic surfactant is a difunctional block-polymer that is a polyoxyalkylene derivative of propylene glycol having a molecular weight of about 25,000, an octoxynol or deoxycholate, and wherein the nonionic surfactant and the stearic acid are present in a ratio of about 1:1 (w:w) to about 10:1 (w:w) to form a suspension in a pharmaceutically acceptable diluent or carrier.

According to another aspect of the invention, there is provided a composition consisting of 10% w/w stearic acid, 5% w/w sucrose stearate, 8% w/w mineral oil NF, 5% w/w propylene glycol USP, 2.7% w/w benzyl alcohol NF and 69.3% purified water USP.

According to another aspect of the invention, there is provided a method of treatment comprising administering to a mammal in need thereof an effective amount of a composition to prevent or treat viral infection, wherein the composition comprises a nonionic surfactant and an active ingredient selected from the group consisting of stearyl alcohol, erucyl alcohol, brassidyl alcohol, arachidyl alcohol, n-docosanol, n-docosane, n-docosanoic acid, erucamide and stearic acid, or mixtures thereof, wherein the nonionic surfactant is a difunctional block-polymer that is a polyoxyalkylene derivative of propylene glycol having a molecular weight of about 1,000 to about 25,000, an octoxynol or deoxycholate, and wherein the nonionic surfactant and the active ingredient are present in a ratio of about 1:1 (w:w) to about 10:1 (w:w) in a pharmaceutically acceptable diluent or carrier. In one embodiment of the method, the viral infection for treatment is caused by a herpes simplex virus, cytomegalovirus, Epstein-Barr virus, varicella zoster virus, influenza virus, human lymphotrophic virus, human immunodeficiency virus, papilloma virus or respiratory syncytial virus. In another embodiment the composition is administered topically, preferrably administered three to five times per day. In other embodiments, the composition used in the method is administered parenterally or by transmembranal penetration.

According to another aspect of the invention, there is provided a method of treatment comprising administering an effective amount of a composition to a mammal in need thereof to relieve skin or membrane inflammation, wherein the composition comprises a nonionic surfactant and an active ingredient selected from the group consisting of stearyl alcohol, erucyl alcohol, brassidyl alcohol, arachidyl alcohol, n-docosanol, n-docosane, erucamide and stearic acid, or mixtures thereof, wherein the nonionic surfactant is a difunctional block-polymer that is a polyoxyalkylene derivative of propylene glycol having a molecular weight of about 1,000 to about 25,000, an octoxynol or deoxycholate, and wherein the nonionic surfactant and the active ingredient are present in a ratio of about 1:1 (w:w) to about 10:1 (w:w) in a pharmaceutically acceptable diluent or carrier. In one embodiment of this method, the administered composition comprises about 5% to about 20% w/w stearic acid and further comprises a sugar based stearate. In a preferred embodiment, the administered composition comprises about 10% to about 12% w/w n-docosanol and further comprises a sugar based stearate. In another embodiment, the composition is administered topically about three to five times per day, preferably to a burn site. In one more embodiment of the method, the composition is administered by transmembranal penetration.

According to another aspect of the invention, there is provided a composition comprising a nonionic surfactant that is a block copolymer of ethylene oxide and propylene oxide having a molecular weight of about 8,400 combined with n-docosanoic acid, wherein the nonionic surfactant and n-docosanoic acid are present in a ratio of about 5:1 (w:w) in a pharmaceutically acceptable diluent or carrier. This aspect of the invention further includes a method of treatment comprising administering an effective amount of the composition to a mammal in need thereof to inhibit cell growth or proliferation.

It should be understood that both the foregoing general description and the following detailed description are exemplary and explanatory only and are not restrictive of the invention as claimed. The accompanying drawings illustrate various embodiments of the invention and, together with the description, serve to explain the principles of the invention.

BRIEF DESCRIPTION OF THE DRAWINGS

FIG. 2A is a diagram showing that increasing the ratio of surfactant to n-docosanol decreases viral plaque production when Vero cells are incubated with the suspension for 12 hours before adding HSV-2 virus; the surfactant:n-docosanol ratios were 1:1 (■), 3:1 (Δ), 5:1 (♦) and 10:1 (○).

FIG. 2B shows the corresponding controls as in FIG. 2A using the same concentration of surfactant in suspension as for each surfactant:alcohol ratio shown in FIG. 2A but without n-docosanol (using the same symbols as in FIG. 2A).

DETAILED DESCRIPTION OF THE PREFERRED EMBODIMENT

Figure 1:
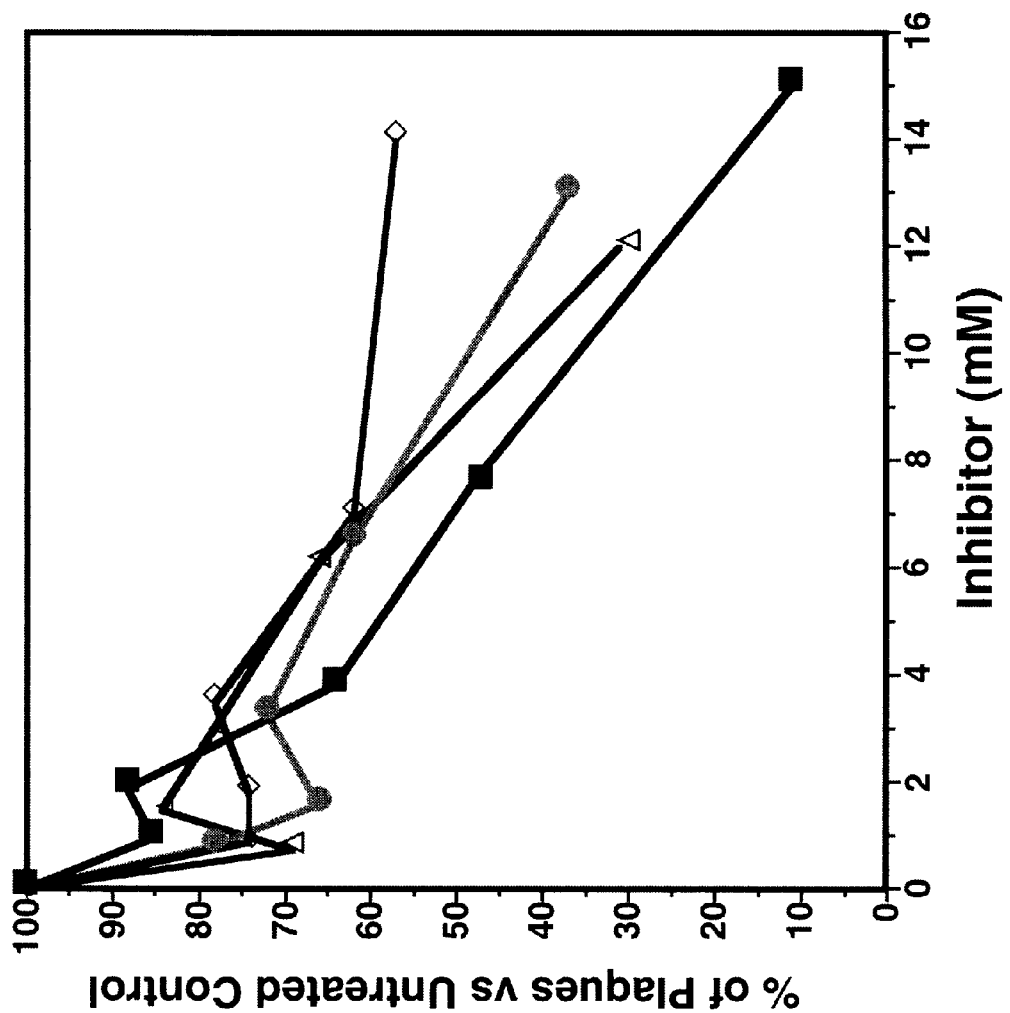
FIG. 1 is a diagram showing inhibition of HSV-2 plaque formation in Vero cells in vitro by suspensions of n-docosanol (C22, ■), n-tetracosanol (lignoceryl) alcohol (C24, ◊), n-hexacosanol (C26, ●) and n-octacosanol (C28, Δ) at the concentrations shown on the X-axis (data is percentage of plaques observed compared to control cultures exposed to surfactant suspensions lacking long-chain alcohol).

Methods of synthesis of n-docosanol and erucyl alcohol (cis-13-docosen-1-ol) are known to those skilled in the art (e.g., see U.S. Pat. No. 4,186,211). Stearyl alcohol can be synthesized according to the method of Brown et al. (*J. Am. Chem. Soc.* 78:2582, 1956). Methods of synthesis of alkanes, aliphatic alcohols, amides and aliphatic acids are well known in the art (e.g., see A. Streitwieser, Jr. & C. H. Heathcock, *Introduction to Organic Chemistry*, 2nd ed., Macmillan Publishing Co., New York, N.Y., 1981, at pages 160, 243–247, 303–307, 311–312, 315–317, 401–406, 447–453, 515–516, 544, 548–555, 604–605, 670, 753–754 and 950).

Compositions of this invention suitable for use in preventing or treating viral infections comprise an active ingredient or combination of compounds as the active ingredient, selected from a group consisting of saturated aliphatic alcohols, mono-unsaturated aliphatic alcohols, aliphatic alkanes, mono-unsaturated aliphatic amides and aliphatic acids having a carbon chain length of 18 to 28 carbons (C18 to C28). The preferred composition includes as an active ingredient stearyl alcohol, erucyl alcohol, erucamide, brassidyl alcohol, arachidyl alcohol, n-docosane, n-docosanoic acid and stearic acid, or mixtures thereof, preferably erucyl alcohol, erucamide, brassidyl alcohol, arachidyl alcohol, n-docosane, n-docosanoic acid, stearic acid, or mixtures thereof combined with a surfactant. The surfactant is preferably a nonionic detergent such as a difunctional block-polymer that is a polyoxyalkylene derivative of propylene glycol having m.w. of about 1,000 to about 25,000 or greater. Preferably the surfactant is a block co-polymer of propylene oxide and ethylene oxide (poloxamer 188) having a m.w. of about 8,400 (e.g., PLURONIC F-68®). Other preferred surfactants are octoxynol-9 and/or octoxynol-10 (e.g., TRITON X-100®), deoxycholate or mixtures of nonionic detergents. The active ingredients comprise about 0.1% to about 50% by weight of the final composition, preferably 1% to 10% by weight. The optimum antiviral activity of the active ingredients depends on the ratio of surfactant to active ingredient which may range from 1:1 (w:w) to 10:1 (w:w), and preferably is 5:1 (w:w).

Methods of suspending aliphatic alcohols, long-chain fatty acids and long-chain alkanes are well known in the art. One suitable method of making such a suspension is dilution of a nonionic detergent surfactant to 1 to 100 mg/ml in water or an aqueous solution such as a physiological saline solution and heating the solution (e.g., 37° C. to 50° C.). The active ingredient is then added to this surfactant solution to produce the desired final concentration of active ingredient and the combination is mixed (e.g., rotary or reciprocal mixing, stirring or sonicating), to produce a suspension of globular particles (about 0.1μ to 100μ average size). Other acceptable carriers include emulsions (oil-in-water or waterin-oil), solutions, creams, lotions, ointments, foams, gels and aerosols, all of which can be prepared using well-known methods.

The active agents and surfactants are combined with a carrier that is physiologically compatible with the skin and membrane tissue of a human or animal to which it is administered. That is, the carrier is substantially inactive except for surfactant properties used in making a suspension of the active ingredients. The compositions may include other physiologically active constituents that do not interfere with the efficacy of the saturated aliphatic alcohols, mono-unsaturated aliphatic alcohols, aliphatic alkanes and aliphatic acids. An exemplary composition is disclosed in U.S. Pat. No. 3,592,930.

Suitable carriers include aqueous and oleaginous carries such as, for example, white petrolatum, isopropyl myristate, lanolin or lanolin alcohols, mineral oil, sorbitan monooleate, propylene glycol, cetylstearyl alcohol (together or in various combinations), with a detergent (e.g., polyoxyl stearate or sodium lauryl sulfate) and mixed with water to form a lotion, gel, cream or semi-solid composition. Other suitable carriers comprise mixtures of emulsifiers and emollients with solvents such as sucrose stearate, sucrose cocoate, sucrose distearate, mineral oil, propylene glycol, 2-ethyl-1,3-hexanediol, polyoxypropylene-15-stearyl ether and water. Preservatives may also be included in the carrier including methylparaben, propylparaben, benzyl alcohol and ethylene diamine tetraacetate salts. Dilute suspensions without thickeners are most suitable for delivery to skin surfaces as aerosol sprays, using well known methods of delivery. The composition may also include a plasticizer such as glycerol or polyethylene glycol (m.w. 800 to 20,000) and penetrants such as azone. The composition of the carrier can be varied so long as it does not interfere with the pharmacological activity of the active ingredients.

The compositions may also include anti-microbial agents, other antiviral agents, anti-fungal agents, antioxidants, buffering agents, sunscreens and cosmetic agents such as coloring agents, fragrances, lubricants and moisturizers or drying agents. Antimicrobial agents useful for inclusion in the compositions include polymyxin B and tetracycline. Other antiviral agents included in the formulations may be nucleoside analogs such as acyclovir or cytokines. Antifungal agents that may be included are micatin or tolnaftate. Antioxidants such as vitamin E may be included. Sunscreens such as para-aminobenzoic acid may be included. Drying agents that may be included are well known, such as, for example, phenol and benzyl alcohol. Lubricants such as synthetic or natural beeswax may also be included. Thickening agents added to the compositions may include pullulin, xanthan, polyvinylpyrrolidone or carboxymethylcellulose.

Optimally the compositions effectively reduce the viral titre overall in the treated individual, particularly for systemic treatment, and in lesions, particularly for topical treatment of affected areas of the skin or mucous membrane. The disclosed methods of treatment also reduce symptoms of viral infection (e.g., pain associated with viral-caused lesions) and promote more rapid healing than seen without treatment.

The method of the present invention includes administration of a composition containing the active ingredient and a surfactant to a human or animal to treat or prevent viral infection. Administration is preferably to the skin or a mucous membrane using a cream, lotion, gel, ointment, suspension, aerosol spray or semi-solid formulation (e.g., a suppository), all formulated using methods well known in the art. Applications of the compositions containing the active ingredient and surfactant effective in preventing or treating a viral infection consist of one to ten applications of 10 mg to 10 g per application for one to fourteen days. Applications are generally once every twelve hours and up to once every four hours. Preferably two to four applications of the composition per day, of about 0.1 g to 5 g per application, for one to seven days are sufficient to prevent or treat a viral infection. For topical applications, the compositions are preferably applied to lesions daily as soon as symptoms (e.g., pain, swelling or inflammation) are detected.

The compositions and methods are useful for preventing or treating a variety of viral infections such as those caused by herpes viruses including HSV-1, HSV-2 and HSV-6, cytomegalovirus (CMV), Epstein-Barr virus (EBV) and varicella zoster virus (VZV), by influenza viruses, human lymphotrophic viruses (e.g., HTLV-1), human immunodeficiency viruses (e.g., HIV-1), papilloma virus and respiratory syncytial virus. Because of the cytostatic activity of some of the compositions, the compositions and methods are also useful for inhibiting malignant cell growth and/or metastasis. This cellular inhibition can be combined with well known treatments for cancer (e.g., irradiation and/or chemotherapy) to lead to total or partial remission of a tumor or other cancerous cell growth.

Unless defined otherwise, all scientific and technical terms used herein have the same meaning as commonly understood by those skilled in the relevant art. Unless mentioned otherwise, the techniques employed or contemplated herein are standard methodologies well known to one of ordinary skill in the art. The examples of embodiments are for illustration only.

EXAMPLE 1

Antiviral Activity of C21 to C28 Aliphatic Alcohols

Aliphatic alcohols were suspended in the surfactant PLURONIC F-68® (BASF Corp., Parsippany, N.J.) using the following procedure described for the alcohol n-docosanol (>98% pure; from M. Michel, New York, N.Y.). The surfactant was diluted to 10 mg/ml in 37° C. Dulbecco's high-glucose modified Eagle's medium (DMEM; Whittaker Bioproducts, Walkersville, Md.), and the solution was heated to 50° C. n-Docosanol was added to a final concentration of 30 mM to the surfactant solution and the mixture was sonicated for 21 min at an initial output of 65 W using a sonifier (Branson 450) causing the suspension to heat to 88° C. The resulting suspension contains globular particles of about $0.3\mu$ average size as determined by transmission electron microscopy. Control solutions containing PLURONIC F-68® with no added aliphatic alcohol and suspensions containing different concentrations of surfactant and/or n-docosanol were prepared using essentially the same procedure.

Suspensions of stearyl alcohol (C18), arachidyl alcohol (C20), heneicosanol (C21), lignoceryl alcohol (C24), and n-hexacosanol (C26) were prepared using essentially the same protocol as described for n-docosanol suspensions. For aliphatic alcohols longer than C22, the mixtures were heated before sonication to 80° C. for lignoceryl alcohol (C24) and 90° for n-hexacosanol (C26) and 1-octacosanol (C28). n-Hexadecanol was obtained from Aldrich Chemicals (Milwaukee, Wis.); stearyl alcohol and arachidyl alcohol were from M. Michel (New York, N.Y.) and the other compounds were from Sigma Chemical Co. (St. Louis, Mo.).

The MS strain of Herpes simplex virus 2 (HSV-2; from the American Type Culture Collection, Rockville, Md.; ATCC No. VR-540) was used to infect African Green monkey kidney cells (Vero cells; ATCC No. CCL 81) to determine the effects of aliphatic alcohol suspensions on efficiency of plaque formation. Vero cells were cultured using $6 \times 10^5$ cells in 1.8 ml medium per 35-mm well or $3 \times 10^5$ cells in 0.8 ml medium per 16-mm well in DMEM supplemented with 5% fetal calf serum, sodium pyruvate, L-glutamine, penicillin/streptomycin and 1 mM Hepes buffer at 37° C. in a humidified incubator containing 10% $CO_2$. Control surfactant suspensions or suspensions containing aliphatic alcohols were added at the outset of the culture. After 24 hr, HSV-2 virus was added to the cultures using 175 pfu/35-mm well and or 50 pfu/16-mm well.

After about 42 hr from addition of HSV-2, cultures were washed once with a physiological saline solution. The cells were fixed and stained with methanol containing carbol-Fuchsin (1.25 mg/ml) and methylene blue (2.5 mg/ml) and scored for plaques. The data presented are the mean of duplicate cultures, which generally varied by less than 10%, and statistical comparisons were made using Student's t test.

The suspensions containing C21, C24, C26, or C28 aliphatic alcohols inhibited HSV-2 plaque production in Vero cells with dose response curves similar to that of n-docosanol (C22). Typical results are shown in FIG. 1. The effective concentrations (mM) required for 50% inhibition ($EC_{50}$) of plaque production are listed in Table 1.

TABLE 1

Alcohol-Suspension Inhibition of HSV-2 Plaque Formation

| Carbon Chain Length | M.W. | 50% Inhibition* Concentration (mM) |
| --- | --- | --- |
| 18 | 284.6 | Toxic** |
| 20 | 298.6 | Toxic** |
| 21 | 312.6 | 16.0 |
| 22 | 326.6 | 8.6 |
| 24 | 354.6 | 14.1 |
| 26 | 382.6 | 8.4 |
| 28 | 410.6 | 10.5 |

*Percent inhibition of plaque formation by HSV-2 added to Vero cells after 12 hr incubation of cells with the indicated alcohol was plotted as a function of alcohol concentration and the amount required for 50% inhibition was determined by linear regression.
**"Toxic" means the cell monolayer was destroyed by the end of a 12-hour incubation period with a suspension containing at least 1.5 mM of the alcohol; at non-toxic concentrations no significant antiviral activity was recorded.

There was no obvious chain length effect on inhibition of HSV-2 plaque formation. All the C21 to C28 alcohols inhibited HSV-2 plaque production and none of the compounds exhibited significantly greater activity than C22. The odd chain length compound, heneicosanol (C21), also inhibited plaque production by HSV-2 showing that there is no obvious chain length effect (i.e., odd chain length molecules functioned as well as even).

The suspensions of stearyl alcohol (C18) and arachidyl alcohol (C20) were toxic to Vero cells when added in amounts where viral inhibitory activity was observed with n-docosanol. At concentrations that were not cytotoxic (0.2 $\mu$M for stearyl alcohol and 2 $\mu$M for arachidyl alcohol), equivalent concentrations of the C18 and C20 aliphatic alcohols showed no inhibition of viral plaque production. Control suspensions of surfactant lacking an aliphatic alcohol were not cytotoxic and did not exhibit antiviral activity.

EXAMPLE 2

Effects of Increasing the Ratio of Surfactant to Aliphatic Alcohol

The antiviral effect of increasing the ratio (w:w) of surfactant to aliphatic alcohol was demonstrated using increasing ratios of PLURONIC F-68® to n-docosanol (compare to Example 1 using a 1:1 (w:w) ratio of surfactant to alcohol). The 1:1 suspension has a molecular ratio of 26:1 for n-docosanol (m.w. 326.57) to surfactant (m.w. 8,400) molecules. Generally, increasing the amount of surfactant decreases the particle size in suspension and causes formation of smaller unilamellar, rather than multilamellar, vesicles (Sandra, A. and R. E. Pagano, *J. Biol. Chem.* 254:2244–2249, 1979). This results in more of the alcohol occurring at the particle surface where it is available for interaction with cells.

Suspensions of n-docosanol were made essentially as described in Example 1 using a constant amount of the alcohol but increasing the amount of surfactant to achieve a 3:1, 5:1 and 10:1 (w:w) ratio of PLURONIC F-68® to n-docosanol in the final suspension. Increasing the surfactant to alcohol ratio increased the antiviral effectiveness of the suspension in Vero cell culture (FIG. 2). That is, the 3:1 surfactant to alcohol ratio suspension showed greater antiviral activity than the 1:1 ratio (at n-docosanol $\geq 8$ mM); the 5:1 ratio suspension showed increased antiviral activity compared to the 1:1 ratio (at n-docosanol $\geq 4$ mM); and the 10:1 ratio exhibited more antiviral activity compared to the 1:1 ratio (at n-docosanol $\geq 1$ mM). The antiviral activity was dependent on the n-docosanol in the suspension because control cultures incubated with the same concentration of surfactant in suspension as for each of the ratio tested above showed essentially no antiviral activity (FIG. 2B).

The increased surfactant to alcohol ratio also correlated with an increase in the amount of cell-associated n-docosanol as determined using Vero cells incubated for 24 hours with surfactant-n-[$1-^{14}$C]docosanol suspensions. Cells incubated with suspensions containing a 4:1 ratio of surfactant to n-docosanol bound $7.8 \times 10^{-6}$ $\mu$g/cell, whereas an equivalent culture incubated with a 1:1 ratio suspension bound $3.1 \times 10^{-6}$ $\mu$g/cell. Optimal antiviral activity of n-docosanol was obtained with surfactant to alcohol ratios of about 4:1 to 5:1 (w:w).

The antiviral activity of the aliphatic compounds was not a property of a unique combination of the aliphatic compound and a particular nonionic surfactant in suspension. That is, other detergents produced effective antiviral suspensions of aliphatic alcohol. Suspensions of n-docosanol with a non-ionic octoxynol detergent (TRITON X-100®, Rohm & Haas) were prepared by: a) melting 2.5 g of n-docosanol with 1.5 g detergent at 90° C., b) mixing the melted solution with 500 ml saline at 90° C. and 1.15 g polyvinylpyrrolidone (PVP), c) processing the hot mixture through a microfluidizer at 1300 psi for 5 cycles, and d) ultrafiltering the processed mixture through a hollow fiber cartridge to eliminate excess detergent and PVP. A control detergent suspension was prepared in a similar manner except that n-docosanol was omitted. Deoxycholate suspensions of n-docosanol (surfactant to alcohol ratio of 1:1 by weight) were prepared essentially as described above.

Figure 3:
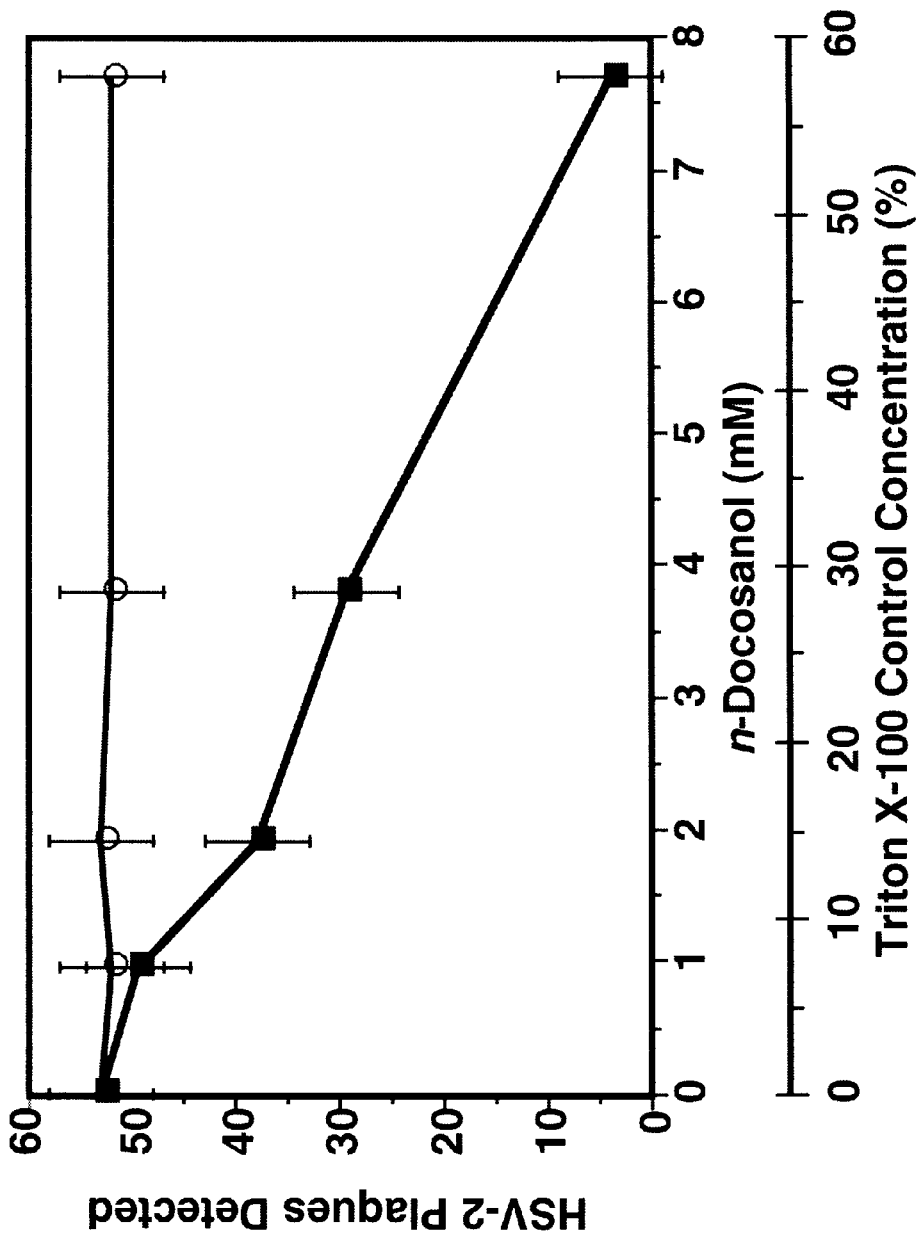
FIG. 3 is a diagram showing that octoxynol surfactant suspensions of n-docosanol (■) inhibit HSV-2 plaque formation in Vero cells incubated with the suspension and HSV-2 for 48 hours with increasing inhibition correlated with increasing concentration of n-docosanol, whereas control cultures incubated with HSV-2 and octoxynol surfactant (○) showed no inhibition (i.e., equivalent to untreated controls having about 50 plaques/well); bars above and below the data points show the standard deviation for duplicate samples.

Both the octoxynol and deoxycholate suspensions of the n-docosanol inhibited HSV-2 plaque production in the Vero cell assay. Typical results are shown in FIG. 3. The octoxynol/n-docosanol suspension inhibited plaque formation relative to the octoxynol control at n-docosanol concentrations of greater than or equal to 2 mM with an $EC_{50}$ of about 4.5 mM. The nonionic surfactant used to make an aliphatic alcohol suspension does not account for the suspension's antiviral activity.

Increasing the ratio of surfactant to n-docosanol significantly increased the antiviral activity of the suspension. That is, the amount of n-docosanol in the suspension required for 50% inhibition of plaque production decreased (e.g., from 15 mM to 3 mM).

EXAMPLE 3
Antiviral Activity of the Aliphatic Alkane, n-Docosane

A surfactant/n-docosane (Sigma Chemical Co.) suspension was prepared essentially as described in Example 1. The antiviral activity of the surfactant/n-docosane suspension was compared to that of a similar surfactant/n-docosanol suspension using the Vero cell assay to measure inhibition of HSV-2 plaque formation essentially as described in Example 1.

Figure 4:
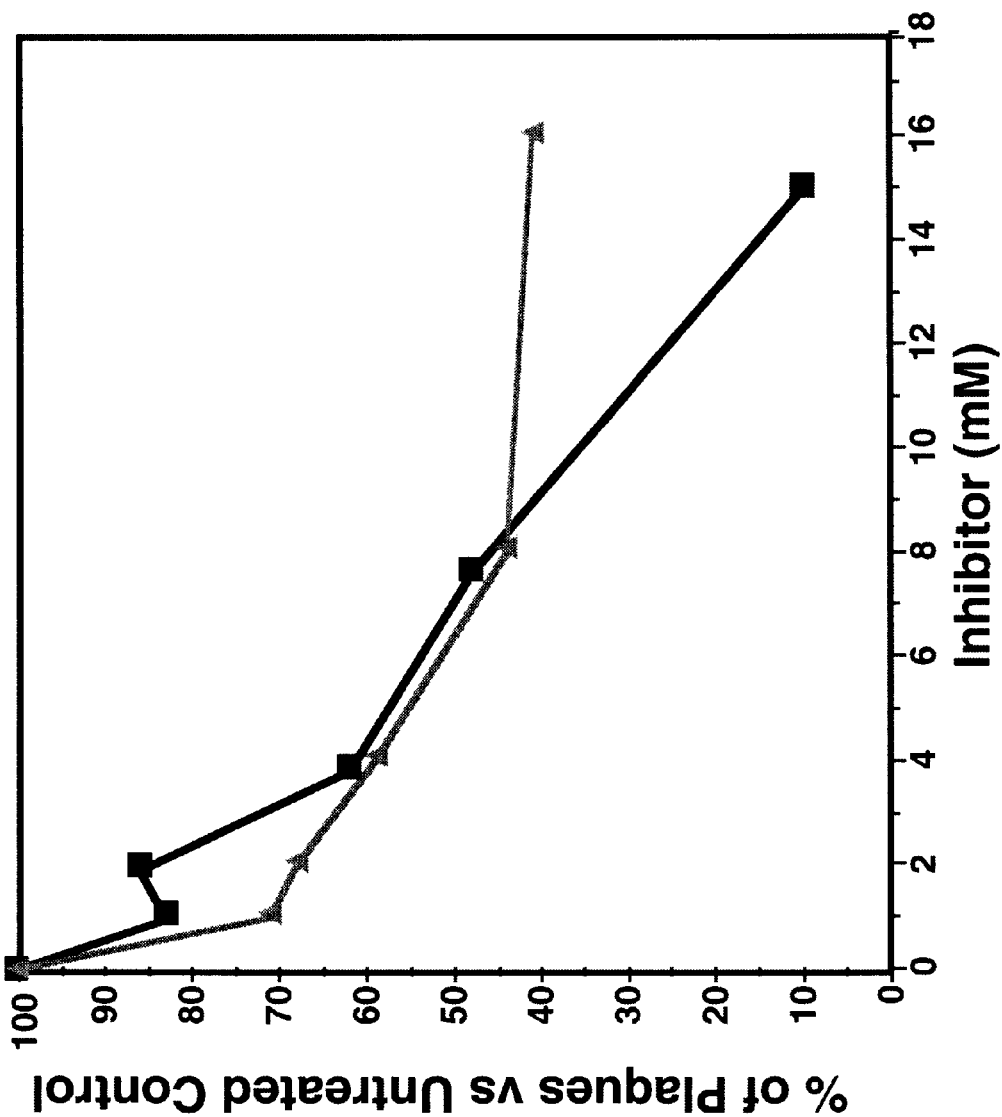
FIG. 4 is a diagram showing that suspensions of surfactant/n-docosanol (■) and surfactant/n-docosane (Δ) inhibit HSV-2 viral plaque formation in cultured Vero cells incubated with the compounds for 12 hours before the addition of HSV-2.

As shown in FIG. 4, a surfactant/n-docosane suspension inhibited plaque production by HSV-2 in Vero cell cultures with a dose response curve similar to that of the surfactant/n-docosanol suspension. PLURONIC F-68® suspensions of n-docosanol (■) and n-docosane (Δ) inhibited HSV-2 viral plaque formation in cultured Vero cells incubated with the suspensions for 12 hours before the HSV-2 addition. Control surfactant suspensions showed no antiviral activity (data not shown). Hence, both the C22 aliphatic alcohol and alkane exhibited comparable antiviral activity indicating that the hydroxyl moiety was not required for the activity as measured by inhibition of viral plaque formation.

EXAMPLE 4
Oxidation of the 1-hydroxyl Moiety of n-Docosanol Results in Cytotoxicity A nonionic detergent surfactant/n-docosanoic acid (Sigma Chemical Co.) suspension was prepared and tested for antiviral activity using Vero cells and HSV-2 essentially as described in Example 1. The C22 fatty acid was toxic to Vero cells when used at concentrations equivalent to those at which viral inhibition occurs with n-docosanol (see Table 2). When suspensions of n-docosanoic acid at 4 mM to 15 mM were added to the cultures, the cells became rounded and detached from the plate. At tolerable concentrations of n-docosanoic acid ($\leq 2$ mM), the antiviral activity was approximately equal to that observed with n-docosanol suspensions at the same concentrations, but significantly less than that observed with 4 to 15 mM n-docosanol suspensions. Thus, the C22 fatty acid exhibits some antiviral activity at dilutions tolerable to cells but has increased cytotoxicity compared to the corresponding aliphatic alcohol.

TABLE 2

| | Percent Inhibition of Plaque Formation** | | | | |
|---|---|---|---|---|---|
| Conc* | Docosanol | Docosane | Docosanoic acid | Erucyl Alcohol | Brassidyl Alcohol |
| 15 | 66 | 58 | Toxic† | Toxic | ND |
| 8 | 44 | 55 | Toxic | Toxic | 48 |
| 4 | 36 | 42 | Toxic | Toxic | 44 |
| 2 | 40 | 31 | 30 | Toxic | 35 |
| 1 | 14 | 28 | 16 | 93 | 27 |

TABLE 2-continued

| | Percent Inhibition of Plaque Formation** | | | | |
|---|---|---|---|---|---|
| Conc* | Docosanol | Docosane | Docosanoic acid | Erucyl Alcohol | Brassidyl Alcohol |
| 0.5 | ND‡ | ND | 26 | 91 | ND |
| 0.25 | ND | ND | ND | 70 | ND |

*The mM concentrations of n-docosanol (m.w. 326.6), n-docosane (m.w. 310.6), n-docosanoic acid (m.w. 340.6) and erucyl alcohol (m.w. 324.6) in suspension with PLURONIC F-68 ® (m.w. 8,400) or brassidyl alcohol (m.w. = 324.6) in suspension with TETRONIC-908 ® (m.w. 25,000) in the Vero cell culture 12 hr before addition of HSV-2 virus, except for erucyl and brassidyl alcohol suspensions which were added with the virus.
†"Toxic" means the cell monolayer was destroyed within 24 hr after addition of the suspension at the concentrations of alcohol or acid shown in the first column.
‡"ND" means not determined.
**Inhibition was relative to a control infection of Vero cells to which no suspension was added. Another control was a surfactant suspension to which no active ingredient was added, which, when added to infected Vero cells, showed $\leq 5\%$ inhibition relative to viral infection of Vero cells with no suspension added.

EXAMPLE 5
Antiviral Activity of C22 Mono-unsaturated Aliphatic Alcohols

Surfactant/erucyl alcohol (cis-13-docosen-1-ol; Sigma Chemical Co.) suspensions were prepared and tested for antiviral activity using Vero cells and HSV-2 essentially as described in Example 1 to determine the effect of unsaturation of the hydrocarbon chain. The surfactant/erucyl alcohol suspension was toxic to Vero cells when added to cultures at concentrations where n-docosanol is effective (2–15 mM). However, as shown in Table 2, concentrations that were tolerable to the cells ($\leq 1$ mM) showed significant inhibition of HSV-2 plaque production (to 93%). Moreover, no cellular toxicity was observed at 1 mM erucyl alcohol. The effective concentration required to inhibit plaque formation by 50% for erucyl alcohol ($EC_{50}$=0.15 mM) was 60-fold lower than the concentration required for n-docosanol ($EC_{50}$=9 mM). Thus, the therapeutic index is greater than or equal to 6.7 (i.e., 1 mM/0.15 mM).

Similarly, the antiviral activity of the trans-isomer of the C22 mono-unsaturated alcohol, brassidyl alcohol (trans-13-docosen-1-ol) was determined. Suspensions were made with another non-ionic surfactant, TETRONIC-908® (BASF) and viral inhibition assays were performed with HSV-1 instead of HSV-2 using the procedures essentially as described in Example 1. As shown in Table 2, brassidyl alcohol exhibits antiviral efficacy similar to n-docosanol. The cellular toxicity of brassidyl alcohol was significantly less than that of erucyl alcohol.

Based on these results, the addition of a single cis (but not trans) double bond at position 13 of the C22 aliphatic alcohol greatly increased antiviral activity. The alcohol with the trans double bond was less toxic than the alcohol with the cis double bond. The increased cytotoxicity may result from the bend in the molecule resulting from the cis double bond.

Surfactant/erucyl alcohol suspensions did not have a direct virucidal effect. That is, incubation of the HSV-2 virus with the surfactant/erucyl alcohol suspension for 2 hours did not inactivate the virus as measured by subsequent plaque formation on Vero cells.

EXAMPLE 6
Erucamide Testing in Mammalian Cell Cultures

Erucamide (cis-13-docosenoamide; m.w.=337.59) is a C22 long-chain amide with a single double bond similar in structure to erucyl alcohol. A nonionic detergent surfactant/ erucamide (Aldrich Chemical Co.) suspension was prepared with TETRONIC-908® and tested for antiviral activity using Vero cells and HSV-2 essentially as described in Example 1. The C22 amide was toxic to Vero cells when used at 3 mM or greater concentrations, similar to the toxicity seen with erucyl alcohol and n-docosanoic acid (see Table 2). When suspensions of erucamide at 3 mM to 15 mM were added to the cultures, the cells became rounded and detached from the plate. At lower concentrations of erucamide in the suspension, significant antiviral activity was seen. At tolerable concentrations of erucamide ($\leq 1.7$ mM), the antiviral activity of the erucamide suspension was less than essentially equivalent concentrations of suspensions of erucyl alcohol but greater than that of suspensions of n-docosanol, n-docosane, n-docosanoic acid or brassidyl alcohol. That is, the percent inhibition of plaque formation for erucamide suspensions was 78% at 1.7 mM, 68% at 1.5 mM, 58% at 1.2 mM, 44% at 0.89 mM, 42% at 0.59 mM and 34% at 0.03 mM. Thus, the C22 amide exhibits significant antiviral activity at dilutions tolerable to cells but has increased cytotoxicity relative to the C22 saturated aliphatic alcohol (n-docosanol) and similar to that seen with the corresponding C22 mono-unsaturated erucyl alcohol.

EXAMPLE 7
Cytotoxicity in Mammalian Cell Cultures n-Docosanol exhibits minimal cytotoxicity to cultured cells even with prolonged incubations. Three assays were used to quantitate the effects of aliphatic alcohols on cell survival and proliferation: 1) counting cells with a hemocytometer and determining the number of cells that exclude trypan blue; 2) measuring the incorporation of $^3$H-thymidine into cellular DNA by adding $^3$H-thymidine (from New England Nuclear) to the culture medium, lysing the cells with water and harvesting the DNA onto filter paper; and 3) measuring total cellular protein using a sulforhodamine assay adapted for use in 96-well microtiter plates (Skehan, P. et al., *J. Natl. Cancer Inst.* 82:1107–1112, 1990). All of these methods are well known cell viability and cytotoxicity assays.

Cells tested include Vero cells (see Example 1), WI-38, a human embryonic diploid lung cell lines (ATCC No. CCL 75), HFL1, a human fetal lung diploid cell line (ATCC No. CCL 153), and a human fetal foreskin (ATCC No. 1635). A murine B-cell hybridoma line (designated MBI-9) was constructed and cultured as described previously (Marcelletti, J. F. et al., *J. Immunol.* 148:3857–3863, 1992) although other tumor lines and hybridomas such as any of the ATCC TIB or HB cell lines could be equivalently used to determine the effects of aliphatic compounds in suspension on cell proliferation. All cells were cultured in DMEM supplemented with 10% fetal calf serum, sodium pyruvate, L-glutamine and penicillin/streptomycin using procedures well known in the art. The suspensions of aliphatic alcohols were prepared essentially as described in Example 1.

Using the first assay, Vero (Green monkey kidney) cells were cultured up to 72 hours in the presence of 9 mM n-docosanol contained in surfactant suspensions without observable deleterious effects when cultures were inoculated at $6 \times 10^5$ cells in 1.8 ml medium per 35-mm well or $3 \times 10^5$ cells in 0.8 ml medium per 16-mm well. Typical data are presented in Table 3, showing that the total number of viable Vero cells and foreskin fibroblasts was unchanged after 24 hr to 72 hr incubation with the aliphatic alcohol suspension. The other cell lines tested, including normal skin fibroblasts (ATCC CRL 1900), WI-38 lung cells, human fetal lung cells and a B-cell hybridoma, exhibited similar cell viability in the presence of n-docosanol suspensions if cells were inoculated at relatively high densities. Control suspensions of surfactant without the aliphatic alcohol also showed no cytotoxicity for the Vero cells but exhibited a time dependent cytotoxicity for the fetal foreskin cells that was not observed with the alcohol-containing suspension. For the fetal foreskin cell line, the addition of the aliphatic alcohol apparently decreased the cytotoxic effects of the surfactant.

TABLE 3

Cell Viability Following Exposure to Surfactant Suspensions With or Without n-Docosanol

| Treatment* | Incubation (hr) | Vero Cells No. Viable** | % Control*** | Fetal Foreskin Cells No. Viable** | % Control*** |
|---|---|---|---|---|---|
| n-docosanol + surfactant | 24 | $7.48 \times 10^5$ | 101 | $2.41 \times 10^5$ | 131 |
| n-docosanol + surfactant | 48 | $8.69 \times 10^5$ | 137 | $2.78 \times 10^5$ | 118 |
| n-docosanol + surfactant | 72 | $8.61 \times 10^5$ | 120 | $2.72 \times 10^5$ | 118 |
| surfactant | 24 | $7.1 \times 10^5$ | 95.7 | $1.55 \times 10^5$ | 84 |
| surfactant | 48 | $7.2 \times 10^5$ | 107 | $1.66 \times 10^5$ | 70 |
| surfactant | 72 | $6.6 \times 10^5$ | 89.0 | $1.0 \times 10^5$ | 43 |

*Vero or fetal foreskin cells were incubated with 9 mM n-docosanol suspended in 1.4 mM surfactant or incubated with medium containing 1.4 mM surfactant. The ratio of surfactant to n-docosanol in the suspension was 4:1 (w:w).
**After the indicated time of incubation, cells were trypsinized and the number of viable cells determined by trypan blue exclusion.
***Control samples were incubated in the presence of media only.

Although the cell lines remained impermeable to trypan blue even after 72 hours of incubation with n-docosanol, normal skin fibroblasts, foreskin fibroblasts, WI-38 cells and human fetal lung cells showed a detectable change in morphology when examined using light microscopy. After 72 hr incubation with the alcohol suspensions, numerous translucent areas appeared in the cells' cytoplasm and the cells appeared vacuolized. Cells treated with control surfactant suspensions did not appear vacuolized after 72 hrs incubation.

In contrast to lack of cytotoxicity generally seen with the n-docosanol suspensions, suspensions of stearyl alcohol (C18) and arachidyl alcohol (C20) were extremely cytotoxic to all cell lines tested. In the presence of these C18 and C20 aliphatic alcohols, cells growing in a monolayer detached from the plate and lysed. Suspended cells also lysed when exposed to the stearyl and arachidyl alcohol suspensions.

Figure 5:
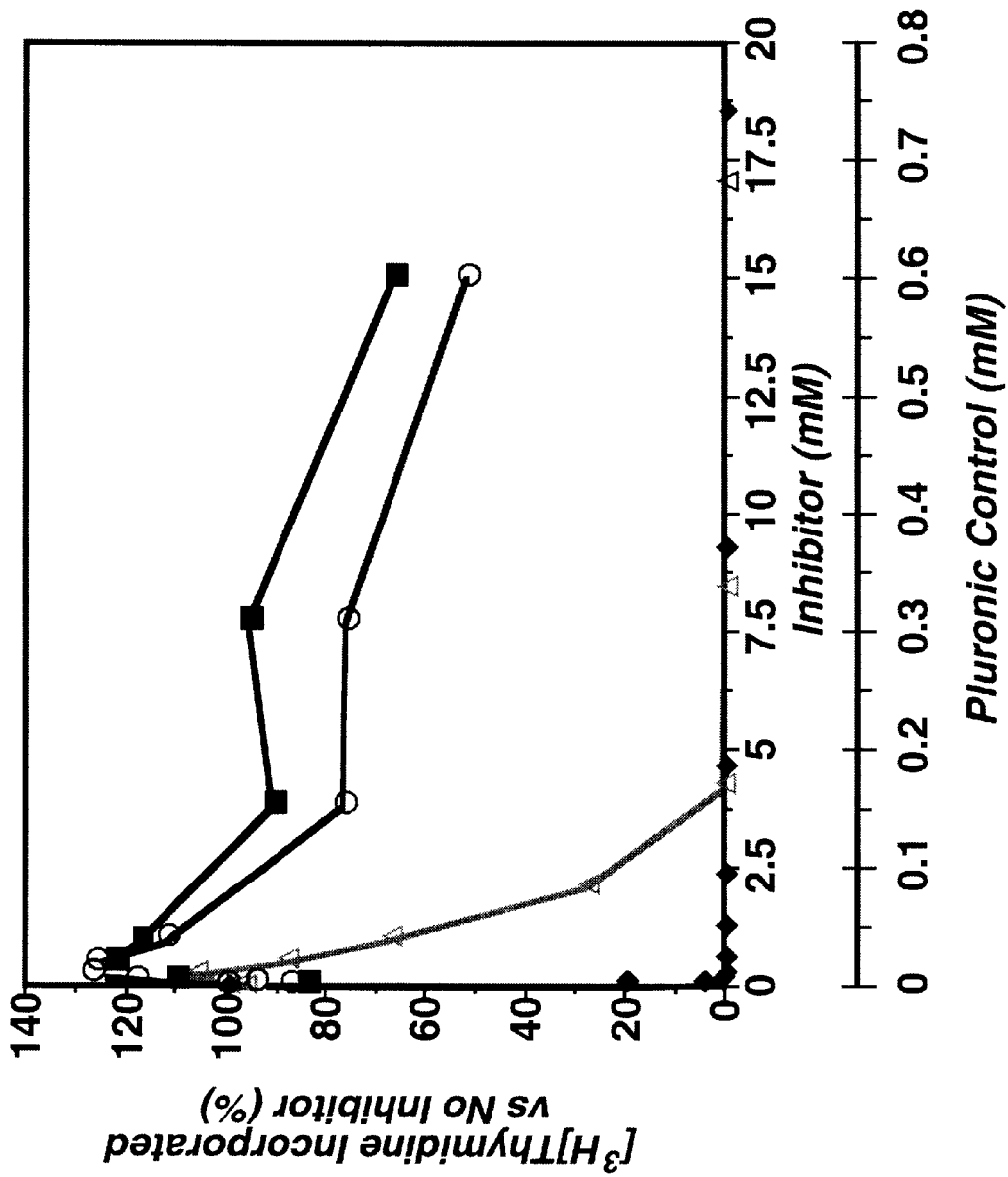
FIG. 5 is a diagram showing that suspensions of stearyl alcohol (C18, ♦) and arachidyl alcohol (C20, Δ) are toxic to cultured B-cell tumor cells incubated for 48 hours with the suspensions at the concentrations indicated on the X-axes compared to controls incubated with suspensions of surfactant without alcohol (○) or surfactant/n-docosanol (C22, ■) as determined by $^3$H-thymidine incorporation into DNA (data is the percentage of controls incubated with media only).

Viability was quantified in a variety of cell lines either by measuring $^3$H-thymidine incorporation into DNA or by measuring total cellular protein by staining with sulforhodamine B. Typical results are illustrated in FIG. 5 showing inhibition of $^3$H-thymidine incorporation into DNA of a B cell hybridoma at different concentrations of the C18, C20 and C22 aliphatic alcohols. The $IC_{50}$ for stearyl alcohol (C18) for the B cell line and the other cell lines was less than 35 $\mu$M; for arachidyl alcohol (C20) the $IC_{50}$ was approximately 1.7 mM. In contrast, the $IC_{50}$ for n-docosanol estimated by extrapolation is approximately 20 mM and is greater than that observed with surfactant alone. Thus, there was about a 50-fold decrease in $LC_{50}$ when the C20 aliphatic alcohol was shortened by 2 carbons.

The data shown in FIG. 5 were obtained after 48 hr of incubation with the suspensions; however, obvious toxicity was apparent within 24 hours of incubation. Suspensions of heneicosanol (C21) and suspensions of the longer chain alcohols, lignoceryl alcohol (C24), n-hexacosanol (C26), and n-octacosanol (C28) showed the same minimal level of cytotoxicity that was seen with the n-docosanol suspensions.

The effects of n-docosanol and n-docosane suspensions on cell proliferation (cytostasis) were quantitated using the sulforhodamine staining assay on cultures of human foreskin fibroblasts incubated in 96-well plates. The results shown in FIGS. 6A and 6B demonstrate that the inhibitory effects of the n-docosanol suspension were dependent upon the initial cell density of the in vitro cultures, whereas the n-docosane suspensions showed no significant antiproliferative effect compared to the control surfactant suspension at either cell density. The results shown in FIG. 7 demonstrate that cells associated with the n-docosanol suspension showed greater proliferation inhibition depending on the total incubation period. That is, longer incubation resulted in more inhibition of cell proliferation.

Figure 6B:
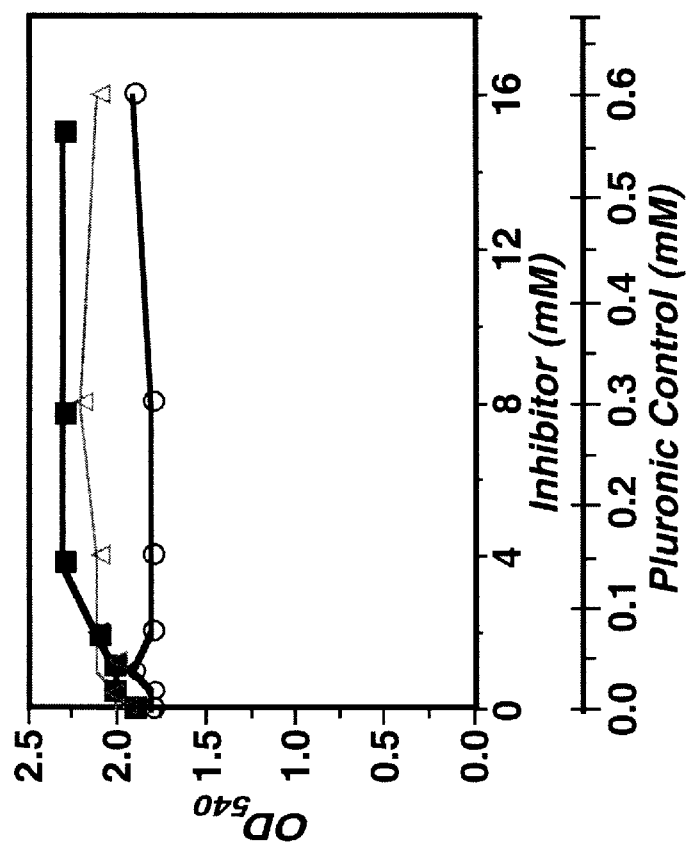
FIG. 6A and FIG. 6B diagrammatically show the cellular antiproliferative effects of suspensions of surfactant/n-docosanol (■) on foreskin fibroblasts compared to cells incubated with suspensions of surfactant/n-docosane (Δ) or with controls incubated with a surfactant suspension without active ingredient (○) at the concentrations shown on the X-axes (averages of duplicate assays quantitated after 96 hours incubation of cells inoculated at 1,000 cells/well (FIG. 6A) or 30,000 cells/well (FIG. 6B) in 96-well plates).
Figure 6A:
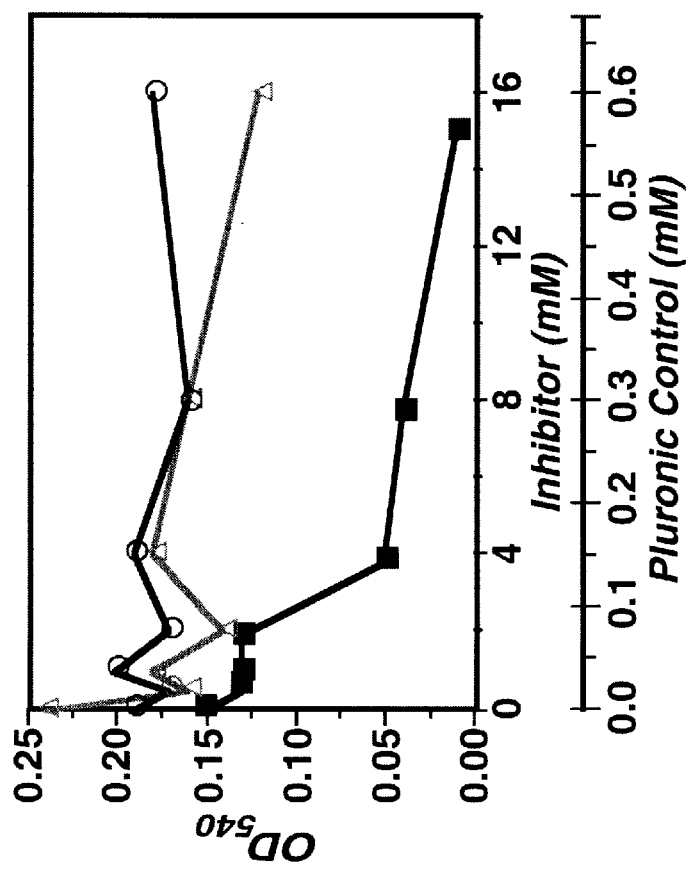
Figure 7:
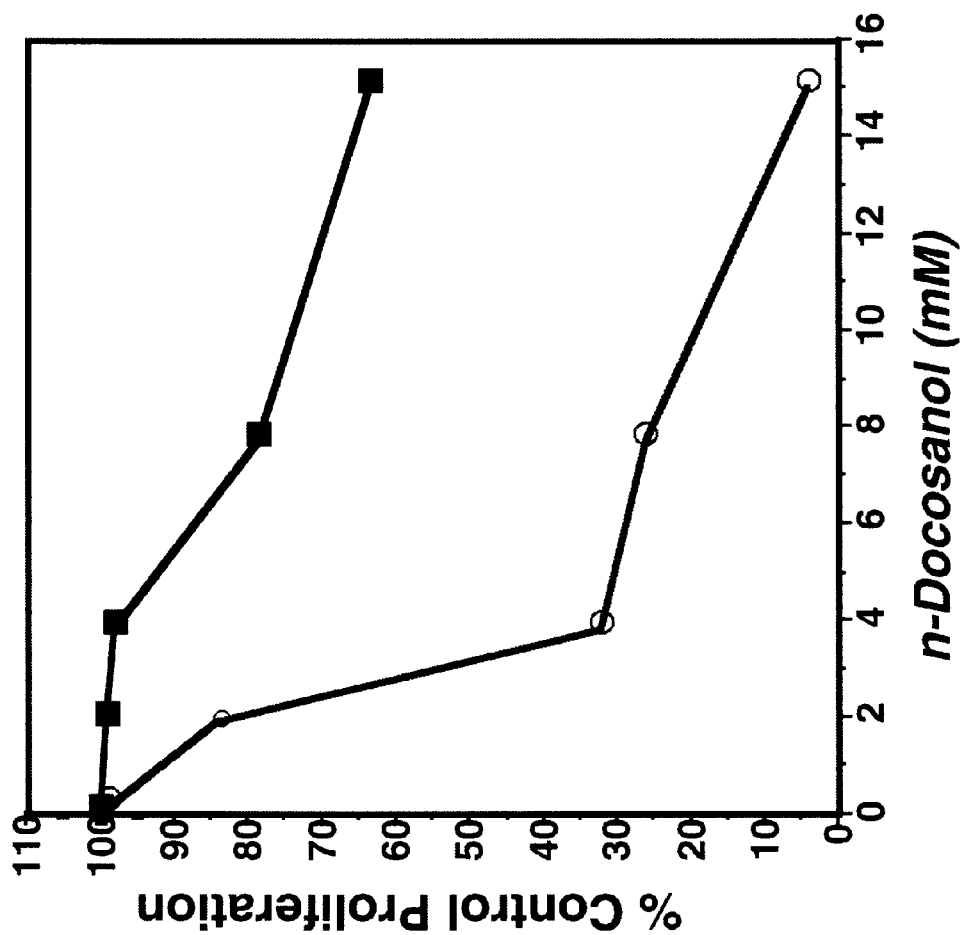
FIG. 7 is a diagram showing the time dependence of cellular antiproliferative effects of surfactant/n-docosanol suspension after 72 hr (■) and 96 hr (○) incubation using the methods as described for FIG. 6A.

Foreskin fibroblasts were plated with or without aliphatic alcohol suspensions or control surfactant suspensions at 1,000 cells/well (FIG. 6A and FIG. 7) or at 30,000 cells/well (FIG. 6B) in 96 well plates. After incubation for 72 hr or 96 hr at 37° C., cells were precipitated with trichloroacetic acid, stained with sulforhodamine and quantitated by measuring the $OD_{540}$ in a microtiter plate reader. FIG. 6 shows the results obtained for cells incubated for 96 hr and FIG. 7 shows the results for cells obtained after 72 hr compared to 96 hr.

Suspensions of greater than 3 mM n-docosanol inhibited proliferation of cells plated at 1,000 cells/well assayed after 96-hours incubation (FIG. 6A). In contrast, the suspension of the C22 alkane, n-docosane, showed minimal antiproliferation effects when compared to the surfactant control (FIG. 6A). At higher initial cell densities (FIG. 6B), or shorter times of incubation (FIG. 7), or at concentrations less than 3 mM, n-docosanol did not inhibit cell proliferation compared to the controls (surfactant only in the suspension). Similar results were observed when n-docosanol was incubated with WI38-cells, human fetal lung cells and normal skin fibroblasts using the same proliferation assay as described for FIGS. 6 and 7.

Suspensions containing aliphatic alcohols greater than C20 exhibited little cellular toxicity. The apparent cytostatic effect was seen only if the cells are plated at low densities and incubated with greater than 3 mM n-docosanol for 72 or more hours. Control suspensions lacking an aliphatic alcohol did not exhibit a cytostatic effect.

Chain length of the aliphatic alcohol affected its cellular toxicity, in contrast to the results presented in Example 1 showing no apparent effect of chain length on antiviral activity. The $IC_{50}$'s decreased from more than 15 mM for C22 or C21 alcohol to 1.5 mM for a C20 alcohol to less than 35 $\mu$M for a C18 alcohol. The significant increase in toxicity with an aliphatic alcohol having a chain length only four carbons shorter than the C22 alcohol was unexpected.

EXAMPLE 8

Antiviral Activity of Stearic Acid Compositions

Antiviral activity and cytotoxicity of stearic acid (m.w. 284.5) dissolved in ethanol or suspended in Tetronic 908®, essentially as described in Example 1, was measured. Antiviral activity was measured as the percentage inhibition of HSV-2 plaque formation in Vero cell culture performed essentially as described in Example 1. Cytotoxicity was assessed by microscopic examination of cells for cell growth and integrity in culture plates compared to untreated control cultures. No apparent toxicity was defined as monolayers of treated cells that were indistinguishable from untreated cells. Moderate toxicity was defined as a thinning of the cell monolayer compared to controls. Toxic was defined as concentrations in which the monolayer of treated cells was destroyed as evidenced by detachment of the cells from the culture plate. No apparent toxicity was observed for 11 $\mu$M and 22 $\mu$M stearic acid suspensions in Tetronic 908 and for 3.5 $\mu$M stearic acid solution in ethanol. All of these treatments showed less than 10% inhibition of HSV-2 plaque formation relative to infected control cell cultures. Moderate toxicity was observed following treatment with a 44 $\mu$M stearic acid-Tetronic 908 suspension and with 35 $\mu$M stearic acid-ethanol solution; antiviral activity could not be quantitated due to condition of the cells. Suspensions and solutions of 88 $\mu$M to 350 $\mu$M stearic acid were all toxic and antiviral activity could not be determined because the monolayer of cells was destroyed.

EXAMPLE 9

Antiviral Activity of Topically Applied Compositions Containing n-Docosanol or Stearic Acid in an Animal Model The antiviral activity of stearic acid containing compositions was confirmed in vivo using a guinea pig model of HSV-2 infection. Hairless guinea pigs (six males per test, 200–300 g each; from Charles Rivers Laboratories, Wilmington, Mass.) were anesthetized and inoculated with HSV-2 (ATCC strain VR-540, grown in Vero cells and purified using standard methods). On day 0 each animal was inoculated in six inoculation sites within a 4 $cm^2$ area of the back with 75 $\mu$l of physiological saline solution containing $9.75 \times 10^6$ PFU/ml. Beginning at 24 hr post-inoculation (day 1), animals were treated topically three or five times daily with creams described below or water as a negative control and treatments continued at these same rates for days 2, 3 and 4. The inoculation sites were evaluated for skin irritation and vesicle formation daily at days 2, 3 and 4. Irritation was scored on a 0 to 4 scale: 0 for normal skin with no erythema; 1, for mild erythema; 2 for moderate erythema; 3 for severe erythema; and 4, for severe erythema accompanied by bleeding. Vesicles are defined as white, fluid-filled pustules.

The compositions for topical treatment were: an n-docosanol containing cream; a stearic acid containing cream; and a placebo. The n-docosanol cream contained 10% w/w n-docosanol (Michel and Co., New York, N.Y.), 5% w/w sucrose stearate (Croda, Inc., New York, N.Y.), 8% w/w mineral oil NF (Witco Corp., Newark, N.J.), 5% w/w propylene glycol USP, 2.7% w/w benzyl alcohol NF (Ruger Chemical Co., Irvington, N.J.) and 69.3% purified water USP. The stearic acid cream contained 10% w/w stearic acid (Henkel, Cincinnati, Ohio), 5% w/w sucrose stearate (Croda, Inc., New York, N.Y.), 8% w/w mineral oil NF (Witco Corp., Newark, N.J.), 5% w/w propylene glycol USP, 2.7% w/w benzyl alcohol NF (Ruger Chemical Co., Irvington, N.J.) and 69.3% purified water USP. Both creams were made by combining all the ingredients except water, heating to 80° C., and stirring the ingredients at 400±5 RPM (using a Heidolph RZR 2051 stirrer), to which the water at 85° C. was added while increasing the stirring rate to 1900±5 RPM. After 3 min at 80° C., the mixture was allowed to cool with continuous stirring to 30° C. (about 8 min). The placebo was made by heating 70% polyethylene glycol (PEG) 400 NF and 30% PEG 3350 NF to 65° C. until the PEG 3350 had completely melted, then stirring the mixture at 400 RPM continuously until the mixture had cooled to 30° C.

The results of these tests are summarized as means in Table 4. Determinations at day 2 were made 48 hr post-inoculation; day 3 at 72 hr post-inoculation; and day 4 at 96 hr post-inoculation (total of six sites per determination). As can be seen from Table 4, at day 2, neither cream affected vesicle number significantly relative to the water-treated control and all sites showed no irritation. At day 3, the n-docosanol cream treated sites showed significant inhibition of the number of vesicles relative to the water-treated control. It appears that three applications per day of n-docosanol containing cream is saturating, because five applications per day gave essentially the same level of inhibition. At day 3, sites treated with the stearic acid cream three times per day showed modest vesicle inhibition compared to the water-treated controls, whereas the sites treated five times per day showed statistically significant inhibition of vesicles. Application of the PEG placebo five times per day did not significantly reduce vesicle numbers relative to the water-treated controls at any time point.

At day 3, some irritation was observed with both the n-docosanol and stearic acid creams. At day 4, treatment three times per day with n-docosanol cream significantly reduced the number of vesicles relative to controls, although minor irritation was observed. At day 4, treatment five times per day with n-docosanol cream or stearic acid cream significantly reduced the number of vesicles relative to controls and placebo, although slight erythema was observed with both treatments.

These in vivo results show that topical treatment of HSV-2 infection with creams containing n-docosanol as the active ingredient or stearic acid as the active ingredient can significantly reduce the number of vesicles resulting from the infection. The cream containing n-docosanol as the active ingredient appears to be more effective at treating viral infections because significant reductions in vesicle numbers were seen with only three treatments per day whereas five treatments per day were needed to see reductions in vesicle numbers with the cream containing only stearic acid as the active ingredient.

TABLE 4

Topical Treatment of HSV-2 in Guinea Pig Model

| Treatment | Number of Vesicles | | | Irritation Score | | |
|---|---|---|---|---|---|---|
| | Day 2 | Day 3 | Day 4 | Day 2 | Day 3 | Day 4 |
| Water | 45 | 34 | 19 | 0 | 0 | 0 |
| n-Docosanol (3X/day) | 40 | 12 | 3 | 0 | 1.2 | 0.8 |
| n-Docosanol (5X/day) | 43 | 5 | 3 | 0 | 1.3 | 1.3 |
| Stearic Acid (3X/day) | 49 | 17 | 11 | 0 | 1.2 | 0.8 |

TABLE 4-continued

Topical Treatment of HSV-2 in Guinea Pig Model

| Treatment | Number of Vesicles | | | Irritation Score | | |
|---|---|---|---|---|---|---|
| | Day 2 | Day 3 | Day 4 | Day 2 | Day 3 | Day 4 |
| Stearic Acid (5X/day) | 49 | 13 | 5 | 0 | 1.7 | 2 |
| Placebo (5X/day) | 41 | 30 | 15 | 0 | 0 | 0 |

EXAMPLE 10

Topical Treatment of Burns

A mouse model of contact dermatitis (burn) was used to test the therapeutic efficacy of topically applied creams containing 5% w/w sucrose stearate and having the active ingredients stearic acid (5%, 10% and 20% w/w) or n-docosanol (10% and 12% w/w), compared to untreated controls or mice treated with the PEG placebo ointment. Creams and the placebo ointment were prepared essentially as described in Example 9. For each group tested, the bellies of CAF-1 mice were shaved and a mixture of phenol and chloroform (1:1 v/v containing 0.2% 2-mercaptoethanol and saturated with 1 M Tris buffer, pH 8) was applied to two denuded sites per mouse (5 $\mu$l/site having an area of about 5–8 mm$^2$/site) and air dried. The burn sites were treated with a cream or the placebo ointment at 0.5, 3 and 6 hr after application of the phenol and chloroform mixture and scored at 8 hr after application of the phenol and chloroform mixture. The burn sites were numerically scored as follows: 0, for normal skin; 1, for slight inflammation; 2, for red skin; 3, for very red skin with a red margin around the site; and 4, for ulceration. Greater or lesser severity of each of these numerical scores were assessed an increase or decrease of 0.33 to 0.5.

The results of these tests are summarized in Table 5.

TABLE 5

Therapeutic Efficacy of n-Docosanol or Stearic Acid Containing Creams in Treatment of Phenol Induced Burns

| Treatment | Number of Sites | Mean Score |
|---|---|---|
| None | 6 | 4.1 |
| Placebo Ointment | 2 | 4.2 |
| 10% n-Docosanol Cream | 4 | 0.9 |
| 12% n-Docosanol Cream | 4 | 1.0 |
| 5% Stearic Acid Cream | 2 | 2.7 |
| 10% Stearic Acid Cream | 4 | 2.1 |
| 20% Stearic Acid Cream | 4 | 1.7 |

These results show that treatments of burns with creams containing stearic acid and n-docosanol significantly reduced lesion severity compared to untreated or placebo treated controls which showed severe erythema and ulceration. The therapeutic benefit of lesion treatments with 5%, 10% or 20% w/w stearic acid creams was consistently less than seen following lesion treatment with comparable doses of 10% or 12% w/w n-docosanol containing creams. For both stearic acid and n-docosanol containing creams, a nonlinear increase in therapeutic effect on burn lesions was observed with increasing concentrations of the active ingredients.

EXAMPLE 11

Antiviral Activity of Topically Applied n-Docosanol and Stearic Acid Containing Compositions in Human Clinical Studies The antiviral activity of stearic acid containing compositions was confirmed in vivo in clinical studies of treatment of oral herpes in 648 immunocompetent patients who initiated treatment within 12 hr of a localized oral herpes episode (i.e., at initial prodrome sensation, erythema or papule but not a vesicle). These patients had a history of acute recurrence of herpes labialis with a reported average duration of untreated episodes lasting 8.9 days (from beginning sensation and/or erythema to complete healing). This duration is consistent with a usual course of 8 to 10 days duration for oral herpes episodes in published reports of the disease (R. J. Whitley, in *Fields Virology* at p. 2316).

In these studies, patients were randomized to receive either creams containing 10% n-docosanal or 10% stearic acid prepared essentially as in Example 9. Patients applied the cream topically to the localized herpes affected area five times per day for a minimum of five days (25 scheduled applications, with reapplication after heavy exercise, showering or bathing, the reapplications not counted as a scheduled application). If the herpes episode continued after five days, the patients continued to apply the cream up to ten days (50 scheduled applications). Only 20 patients continued treatment beyond ten days. The patients kept a diary of application times and lesion pain and itching symptoms and were examined twice per day during the treatment period to assess the effectiveness of treatment.

The criteria used to assess treatment included the time to healing which includes episode abortion (defined as complete resolution of episode-associated symptoms before reaching vesicular stage) or complete healing (defined as absence of crust with no evidence of active lesion, whether or not there was any residual post-lesion skin changes such as erythema, flaking or asymmetry); time to cessation of viral shedding (for study number 1 only); time to reduction in pain; time to cessation of pain; time to cessation of itching; and time to hard crust stage. For comparison, the patients' historical data and published results (S. L. Spruance et al., "The Natural History of Recurrent Herpes Simplex Labialis," *New Eng. J Med.* 297:69–75, 1977) for untreated lesions were used.

Table 6 shows the results of two independent studies (indicated by the numbers in parentheses in the table). These data show that the duration of cold sores decreased significantly to an average of 5.5 days following treatment with either the cream containing n-docosanol or the cream containing stearic acid compared to the patients' reported historical average of 8.9 days duration of untreated cold sores. Thus, the duration was significantly reduced by more than 35% ($P \leq 0.0001$) when patients were treated early in the episode with either the n-docosanol or stearic acid containing cream. Moreover, early-stage treatment with either cream shortened the duration of pain symptoms associated with recurrent herpes episodes from around 6 days when the disease was untreated compared to less than 3 days for treated areas.

TABLE 6

Results of Human Clinical Trials of Topical Treatment of Herpes Labialis.

|  | n-Docosanol Cream Treated | Stearic Acid Cream Treated | Untreated○ |
|---|---|---|---|
| Healing Time (hr§) | (1) 123 ± 4.9 | (1) 124 ± 5.2 | (1) 215 ± 0.4 |
|  | (2) 141 + 5.2 | (2) 143 ± 4.0 | (2) 211 ± 0.4 |
| Cessation of Viral Shedding (hr§) | (1) 47 ± 2.4 | (1) 49 ± 1.9 | 74 to 83* |
|  | (2) ND** | (2) ND |  |

TABLE 6-continued

Results of Human Clinical Trials of Topical Treatment of Herpes Labialis.

|  | n-Docosanol Cream Treated | Stearic Acid Cream Treated | Untreated○ |
|---|---|---|---|
| Reduction in Pain (hr§) | (1) 27 ± 2.3 | (1) 31 ± 3.4 | NR** |
|  | (2) 55 ± 4.1 | (2) 50 ± 3.8 |  |
| Complete Cessation of Pain (hr§) | (1) 63 ± 4.4 | (1) 68 ± 4.5 | 111 to 178* |
|  | (2) 96 ± 5.8 | (2) 86 ± 5.0 |  |
| Cessation of Itching (hr§) | (1) 58 ± 4.9 | (1) 51 ± 3.4 | NR |
|  | (2) 63 ± 5.2 | (2) 76 ± 5.8 |  |
| Hard Crust Stage (hr§) | (1) 61 ± 3.2 | (1) 62 ± 2.5 | NR |
|  | (2) 87 ± 4.4 | (2) 94 ± 4.9 |  |

○The healing times are based on the patients' reported histories; all other entries in this column are taken from S. L. Spruance et al., "The Natural History of Recurrent Herpes Simplex Labialis," New Eng. J. Med. 297:69–75, 1977.
§Reported as mean ± standard error of the mean.
*The range represents the median lesions sizes for lesions less than 77.5 mm$^2$ and lesions greater than 77.5 mm$^2$.
***"ND" means "not done" and "NR" means "not reported."

EXAMPLE 12

Enhanced Healing of HSV-1 Lesions Following Topical Treatment with n-Docosane Formulation Ten patients with past histories of occurrences of facial HSV-1 lesions (cold sores) are given cream formulations of 5.0 mg/ml n-docosane suspended in 20 mg/ml poloxamer block co-polymer surfactant; the cream formulations include 5–8% by weight mineral oil NF as an emollient, 5% by weight propylene glycol USP as a humectant and preservative, 1–3% by weight benzyl alcohol NF as an auxiliary preservative and the balance purified water as an aqueous carrier.

The individuals are instructed to apply the cream to lesions or early inflammations around the mouth when the individual detects a cold sore. The individuals have a past historical mean of ten days duration for cold sores that were untreated, with all untreated cold sores developing into vesicles that eventually scab and heal. The individuals are instructed to apply the cream to affected areas of the skin at least twice daily and up to four times daily. The individuals are also instructed to record the stages of infection (from erythema to papule to vesicle to edema to scab) that they observe and to record subjective observations about pain associated with the HSV-1 lesions.

Each individual treats at least one cold sore during the course of the study. All individuals report a decrease in pain when the cold sores are treated with the n-docosane containing cream relative to past lesions that were not treated. For each individual, the episode duration of the HSV-1 infection compared to past infections decreases by 20% to 60% (i.e., durations of 4 to 8 days, depending on the individual). In at least half of the individuals participating in the study who treat cold sores four times per day with the n-docosane containing cream, cold sores do not progress to the vesicle stage. Instead, when HSV-1 lesions are topically treated at the erythema or papule stage, the lesions generally do not progress beyond the papule stage and heal without further development of the lesion. These results show that n-docosane containing formulations are effective in preventing and treating viral infections when applied topically.

EXAMPLE 13

Treatment of Influenza Infection with Erucyl Alcohol or Erucamide Formulations

An aqueous suspension of 0.15 mM erucyl alcohol in 1.4 mM of a nonionic poloxamer 188 surfactant containing propylene glycol USP (0.5% by weight) and benzyl alcohol NF (2% by weight) as preservatives is prepared in a standard flexible nasal spray bottle capable of producing an aerosol of the suspension when the bottle is squeezed. Similarly, a preparation containing 1.5 mM erucamide is made and produced in nasal spray containers for producing an aerosol of the suspension. The preparations are provided during the flu season to two groups (one for testing erucyl alcohol and one for testing erucamide) of twenty healthy individuals who have not been inoculated against influenza virus in the previous 12 months.

The individuals are instructed to use the suspension that they are provided as a nasal spray one to five times per day (one to two sprays per nostril at intervals of 2–4 hr) when flu symptoms are detected (respiratory congestion, body aches, sensitive eyes, fever, nausea or any combination of these). Individuals are instructed to record their subjective and objective observations of the severity of their flu symptoms (duration of symptoms, body temperature when feverish, duration and severity of body aches) during the period in which they detect symptoms. The individuals are also instructed to record their use of the nasal spray suspension (number of sprays administered and times of administration) during this period. The individuals are requested to summarize their subjective observations of the severity of their flu symptoms when using the surfactant/erucyl alcohol or surfactant/erucamide aerosol compared to past experiences with influenza infections.

About half of the individuals participating in the study who used the surfactant/erucyl alcohol aerosol as directed report a decrease in flu symptoms relative to previous flu episodes. Those who use the aerosol an average of five times per day (one to two sprays per nostril) report greatly diminished respiratory congestion associated with the influenza infection compared to untreated individuals. Those who use the aerosol an average of five times per day report a significant decrease in the frequency of fever (one to three times per flu episode) compared to untreated individuals (two to five times per flu episode) and a significant decrease in the highest recorded body temperature (mean of 37.8° C.) compared to untreated individuals (mean of 38.9° C.). The mean duration of flu symptoms in about half of the individuals treated with the surfactant/erucyl alcohol aerosol is 1.7 days whereas untreated individuals have a mean duration of flu symptoms of 3 days. These results show that a surfactant/erucyl alcohol suspension has a therapeutic antiviral affect when applied to mucous membranes.

Similar results are obtained with patients treated with the erucamide suspension nasal spray. About half of the patients report a decrease in flu symptoms relative to previous flu episodes when they use the surfactant/erucamide spray as soon as symptoms were detected. Most individuals experience greatly diminished respiratory congestion when they use the aerosol an average of three times per day (one to two sprays per nostril) compared to previously experienced flu conditions. Most individuals who use the aerosol an average of three times per day report a single fever episode during the flu symptom period with the average highest recorded body temperature at about 37° C. The mean duration of flu symptoms for individuals using the aerosol at least three times daily is two days compared to untreated individuals with a mean duration of flu symptoms of three days. These results show that an aerosol of a surfactant/erucamide suspension has a therapeutic antiviral affect when applied to mucous membranes of the respiratory system.

EXAMPLE 14
Transmucosal Membrane Treatment of HSV-2 Infection with Brassidyl Alcohol Suppositories containing 8 mM brassidyl alcohol in a nonionic detergent suspension, prepared essentially as in Examples 1 and 5, are formulated by adding anhydrous dextrose (300–400 mg/suppository), vegetable starch (300–400 mg/suppository) and magnesium stearate (5–10 mg/suppository) to produce a mixture that is compressed into suppositories (1–10 g per suppository) for vaginal insertion.

Fifteen HSV-2 infected women with past histories of vaginal and/or perivaginal herpes lesions are provided with the suppositories and instructed to use one to four suppositories per day when herpes lesions or discomfort associated with herpes lesions are detected. The women are instructed to record their observations about the duration of the active infection, the severity of the lesions (erythema, papule, vesicle, edema or scab phases), the relative numbers of lesions detected to past occurrences of active infection, and the subjective degrees of pain or discomfort associated with the active infection episode. The women are instructed to use the suppositories as soon as active infection or symptoms of active infection are detected. The women have a past mean of 12 days duration for lesions that develop into vesicles if untreated.

In all cases, each woman treats at least one episode of active herpes infection during the course of the study. All individuals report a decrease in pain and discomfort when the infection is treated with the suppositories relative to past untreated infection episodes. In all cases, the mean duration of the HSV-2 active infection decreases to 7 to 8 days with suppository treatment with five women reporting a mean duration of 3–4 days. In most cases in which the suppositories were used four times per day and treatment began at the erythema or papule stage, the infection did not progress to the vesicle stage and healed after reaching the papule stage.

Alternatively, the surfactant/brassidyl alcohol suspension is formulated into an ointment containing about 50–80% white soft paraffin which is melted at 60° C. for addition and dispersion of the surfactant/brassidyl alcohol suspension before cooling. The ointment is provided in compressible tubes with the instructions that it be used two to five times daily as needed primarily for external genital treatment of active herpes infections. Individuals are instructed to use a quantity sufficient to cover the HSV-2 lesions in the genital or perivaginal area from one to four times daily as soon as symptoms are detected. At least half of the individuals using the ointment report decreased pain and discomfort, shortened healing time and lesions that do not develop into vesicles before healing.

These results show that surfactant/brassidyl alcohol suspensions have a therapeutic antiviral affect when applied topically to mucous membranes.

EXAMPLE 15
Treatment of EBV Infection (Infectious Mononucleosis) with Long-Chain Aliphatic Alcohol Suspensions Ten young adults (age 14–19 yr) diagnosed with infectious mononucleosis (sore throat, fever, malaise, generalized lymphadenopathy, atypical mononucleosis T-lymphocytes in peripheral blood, a total white cell count of 12,000–18,000 in the blood) are treated systemically with a sterile aqueous suspension of a nonionic detergent surfactant containing 10 mM n-hexacosanol, prepared essentially as in Example 1. The suspension is injected (intramuscular or intravenous) in dosages of 0.001 g/kg to 1 gm/kg of the aliphatic alcohol administered by a physician under clinical conditions. The symptoms of the individuals are then monitored daily for one week and weekly for three months for indications of infectious mononucleosis. All of the individuals test EBV-positive at the end of the study period as determined by detection of anti-EBV antibodies in their serum using standard immunoassays.

All of the individuals show healing of sore throat and fever symptoms within one week of administration of the surfactant/n-hexacosanol suspension and a decrease in the febrile illness symptoms in general within two weeks of administration. Eight of the treated individuals demonstrate a decrease in generalized lymphadenopathy within two to three weeks of administration of the aliphatic alcohol suspension with returned vigor. All treated individuals show a decrease in atypical mononucleosis T-lymphocytes in peripheral blood within four weeks of administration with a normal total white cell count in the blood by two months post-treatment.

Similar results are obtained with EBV-infected individuals showing symptoms of infectious mononucleosis who are treated systemically with suspensions of n-docosanol, lignoceryl alcohol and n-octacosanol at effective concentrations.

These results show that systemic administrations of selected long-chain aliphatic alcohols in aqueous suspensions have a therapeutic antiviral effect.

EXAMPLE 16
Treatment of Lymphoproliferative Disease with Long-Chain Aliphatic Alcohol Suspensions Five patients aged 35 to 55 yrs having Hodgkin's disease (Stage I or II-A lymphocytic-histiocytic form characterized by abundant and diffuse infiltrate of mature lymphocytes admixed with histiocytes in the lymph nodes) are treated with weekly injections of sterile aqueous suspensions of 2 mM n-docosanoic acid in Tetronic-908® prepared essentially as described in Example 1. The dosages were 0.1 mg/kg to 10 mg/kg per administration with the preferred method of treatment by i.v. infusion over the course of 1–2 hr in a physiological salt solution.

Four of the patients given the n-docosanoic acid suspension weekly for a total of eight weeks show a significant improvement in symptoms including a decrease in incidence or absence of significant fever and/or night sweats. Moreover, none of these four patients show weight loss during the course of treatment and two report an increase of about 5% of their body weight. In all four patients that respond positively to treatment, there is no progression of the disease to additional lymph nodes or extralymphatic organs or tissues detected at 12 to 16 weeks after administration of the alcohol suspensions. Similar results are obtained with weekly injections of aqueous suspensions containing a nonionic detergent and 20 $\mu$M stearyl alcohol or 1 mM arachidyl alcohol. These results show that the cytotoxic effects of selected long-chain alcohols can be used to treat cytoproliferative diseases.

Although the present invention has been described in the context of particular examples and preferred embodiments, it will be understood that the invention is not limited to such embodiments. Instead, the scope of the present invention shall be measured by the claims that follow.

We claim:

1. A composition comprising a nonionic surfactant and an active ingredient in a ratio of about 1:1 (w:w) to about 10:1 (w:w), combined in a pharmaceutically acceptable diluent or carrier, wherein the nonionic surfactant is a block polymer having a molecular weight of about 1,000 to about 25,000, an octoxynol or deoxycholate, and wherein the active ingredient is stearyl alcohol, erucyl alcohol, brassidyl alcohol, n-docosane, n-docosanoic acid, erucamide, stearic acid or mixtures thereof.

2. The composition of claim 1, wherein the block polymer is a polyoxyalkylene derivative of propylene glycol, having a molecular weight of about 25,000.

3. The composition of claim 1, wherein the block polymer is a polymer of ethylene oxide and propylene oxide, having a molecular weight of about 8,400.

4. The composition of claim 1, wherein the ratio of nonionic surfactant to active ingredient is about 5:1 (w:w) to about 10:1 (w:w).

5. The composition of claim 1, wherein the nonionic surfactant and the active ingredient are in a ratio of about 5:1 (w:w), wherein the nonionic surfactant is a block polymer of ethylene oxide and propylene oxide, having a molecular weight of about 8,400, and wherein the active ingredient is n-docosanoic acid.

6. A composition consisting of 10% w/w stearic acid, 5% w/w sucrose stearate, 8% w/w mineral oil NF, 5% w/w propylene glycol USP, 2.7% w/w benzyl alcohol NF and 69.3% purified water USP.

7. A method of treatment comprising administering to a mammal in need thereof an effective amount of a composition to prevent or treat viral infection, wherein said composition comprises a nonionic surfactant and an active ingredient in a ratio of about 1:1 (w:w) to about 10:1 (w:w), combined in a pharmaceutically acceptable diluent or carrier, wherein the nonionic surfactant is a block polymer having a molecular weight of about 1,000 to about 25,000, an octoxynol or deoxycholate, and wherein the active ingredient is stearyl alcohol, erucyl alcohol, brassidyl alcohol, n-docosane, n-docosanoic acid, erucamide, stearic acid or mixtures thereof.

8. The method of claim 7, wherein administering step is performed to a mammal having or at risk of having a viral infection caused by a herpes simplex virus, cytomegalovirus, Epstein-Barr virus, varicella zoster virus, influenza virus, human lymphotrophic virus, human immunodeficiency virus, papilloma virus or respiratory syncytial virus.

9. The method of claim 7, wherein said composition is administered topically, parenterally or by transmembranal penetration.

10. A method of treatment comprising administering an effective amount of a composition to a mammal in need thereof to relieve skin or membrane inflammation, wherein said composition comprises a nonionic surfactant and an active ingredient in a ratio of about 1:1 (w:w) to about 10:1 (w:w), combined in a pharmaceutically acceptable diluent or carrier, wherein the nonionic surfactant is a block polymer having a molecular weight of about 1,000 to about 25,000, an octoxynol or deoxycholate, and wherein the active ingredient is stearyl alcohol, erucyl alcohol, brassidyl alcohol, n-docosane, n-docosanoic acid, erucamide, stearic acid or mixtures thereof.

11. The method of claim 10, wherein said composition is administered topically or by transmembranal penetration.

12. A method of treatment comprising administering an effective amount of a composition to a mammal in need thereof to inhibit cell growth or proliferation, wherein said composition comprises a nonionic surfactant and n-docosanoic acid in a ratio of about 5:1 (w:w), and wherein said nonionic surfactant is a block polymer of ethylene oxide and propylene oxide, having a molecular weight of about 8,400.

13. A method of treatment comprising administering an effective amount of a composition to a mammal in need thereof to treat a burn, wherein said composition comprises a nonionic surfactant and an active ingredient, comprising a long chain fatty alcohol or fatty acid, in a ratio of surfactant to active ingredient of about 1:1 (w:w) to about 10:1 (w:w), wherein said surfactant and active ingredient are combined in a pharmaceutically acceptable diluent or carrier.

14. The method of claim 13, wherein the nonionic surfactant is selected from the group consisting of a block polymer having a molecular weight of about 1,000 to about 25,000, an octoxynol, and a deoxycholate.

15. The method of claim 13, wherein the active ingredient is selected from the group consisting of stearyl alcohol, erucyl alcohol, brassidyl alcohol, n-docosane, n-docosanoic acid, erucamide, stearic acid or mixtures thereof.

16. A composition comprising a nonionic surfactant and an active ingredient in a ratio of about 1:1 (w:w) to about 10:1 (w:w), combined in a pharmaceutically acceptable diluent or carrier, wherein said nonionic surfactant is octoxynol-9, octoxynol-10 or a combination thereof, and wherein said active ingredient is selected from the group consisting of stearyl alcohol, erucyl alcohol, brassidyl alcohol, arachidyl alcohol, n-docosanol, n-docosane, n-docosanoic acid, erucamide, stearic acid, and a mixture thereof.

17. A composition comprising a nonionic surfactant and an active ingredient in a ratio of about 4:1 (w:w) to about 10:1 (w:w), combined in a pharmaceutically acceptable diluent or carrier, wherein said active ingredient is stearic acid.

18. A composition comprising a nonionic surfactant and stearic acid in a ratio of about 1:1 (w:w) to about 10:1 (w:w), combined in a pharmaceutically acceptable diluent or carrier, wherein the stearic acid is suspended in the nonionic surfactant.

19. The composition of claim 18, wherein said nonionic surfactant is a block polymer that is a polyoxyalkylene derivative of propylene glycol, having a molecular weight of about 25,000, an octoxynol or deoxycholate.

20. A method of treatment comprising administering an effective amount of a composition to a mammal in need thereof to relieve skin or membrane inflammation, wherein said composition comprises a nonionic surfactant, a sugar-based stearate and stearic acid, wherein the stearic acid comprises about 5% to about 20% (w/w) of said composition.

* * * * *